US009157642B2

(12) United States Patent
Maeng et al.

(10) Patent No.: US 9,157,642 B2
(45) Date of Patent: Oct. 13, 2015

(54) AIR CONDITIONER INCLUDING VIRUS REMOVAL DEVICE

(75) Inventors: Ji Hyoung Maeng, Seoul (KR); Dong Nyung Lim, Seoul (KR); Sang Jun Hong, Seoul (KR); Young Suck Byun, Seoul (KR); Dae Soo Jeong, Seoul (KR)

(73) Assignee: LG INNOTEK CO., LTD., Seoul (KR)

( * ) Notice: Subject to any disclaimer, the term of this patent is extended or adjusted under 35 U.S.C. 154(b) by 364 days.

(21) Appl. No.: 13/271,311

(22) Filed: Oct. 12, 2011

(65) Prior Publication Data

US 2012/0085927 A1    Apr. 12, 2012

(30) Foreign Application Priority Data

| Oct. 12, 2010 | (KR) | 10-2010-0099086 |
| Oct. 12, 2010 | (KR) | 10-2010-0099087 |
| Oct. 12, 2010 | (KR) | 10-2010-0099089 |
| Oct. 12, 2010 | (KR) | 10/2010-0099091 |
| Oct. 12, 2010 | (KR) | 10-2010-0099092 |
| Oct. 12, 2010 | (KR) | 10-2010-0099093 |
| Oct. 12, 2010 | (KR) | 10-2010-0099094 |
| Nov. 3, 2010  | (KR) | 10-2010-0108904 |
| Nov. 3, 2010  | (KR) | 10-2010-0108905 |
| Nov. 3, 2010  | (KR) | 10-2010-0108906 |
| Nov. 3, 2010  | (KR) | 10-2010-0108907 |
| Nov. 3, 2010  | (KR) | 10-2010-0108908 |

(51) Int. Cl.

| F24F 3/16  | (2006.01) |
| F24F 13/28 | (2006.01) |
| A61L 2/10  | (2006.01) |
| F24F 1/00  | (2011.01) |
| A61L 9/20  | (2006.01) |

(52) U.S. Cl.
CPC .............. *F24F 1/0007* (2013.01); *A61L 9/20* (2013.01); *F24F 3/166* (2013.01); *A61L 2209/12* (2013.01); *A61L 2209/14* (2013.01); *F24F 2001/004* (2013.01); *F24F 2003/1667* (2013.01)

(58) Field of Classification Search
CPC ... F24F 1/0007; F24F 3/16; F24F 2003/1667; F24F 2013/228; A61L 2/10; A61L 9/20; A61L 2209/12
USPC ........ 250/1, 455.11, 492.1; 62/78; 359/223.1, 359/212.1, 213.1, 214.1, 197.1, 196.1; 362/277; 355/84; 422/24
See application file for complete search history.

(56) References Cited

U.S. PATENT DOCUMENTS

| 4,644,899 | A  | * | 2/1987  | Glaus           | 118/642   |
| 5,330,722 | A  | * | 7/1994  | Pick et al.     | 96/55     |
| 5,817,276 | A  | * | 10/1998 | Fencl et al.    | 422/24    |
| 5,837,207 | A  | * | 11/1998 | Summers         | 422/121   |
| 6,557,356 | B2 | * | 5/2003  | Underwood       | 62/78     |
| 6,601,970 | B2 | * | 8/2003  | Ueda et al.     | 362/225   |
| 6,797,966 | B2 | * | 9/2004  | Summers et al.  | 250/492.1 |
| 7,040,782 | B2 | * | 5/2006  | Mayer           | 362/350   |

(Continued)

FOREIGN PATENT DOCUMENTS

JP       2007147137 A  *  6/2007

*Primary Examiner* — Jack Berman
(74) *Attorney, Agent, or Firm* — Lowe Hauptman & Ham, LLP

(57) ABSTRACT

A virus removal device with an ultraviolet LED may be provided that includes: an operating member; an ultraviolet LED configured to irradiate ultraviolet light onto an object under an operation of the operating member; and a driving means configured to generate a driving force so that the operating member is moved.

14 Claims, 33 Drawing Sheets

(56) References Cited

U.S. PATENT DOCUMENTS

| | | | |
|---|---|---|---|
| 7,278,272 B2 * | 10/2007 | Huston et al. | 62/78 |
| 7,553,456 B2 * | 6/2009 | Gaska et al. | 422/121 |
| 7,560,706 B1 * | 7/2009 | Castelluccio | 250/455.11 |
| 7,692,170 B2 * | 4/2010 | Gaus et al. | 250/504 R |
| 2005/0112039 A1 * | 5/2005 | Sheehan | 422/186.3 |
| 2008/0142435 A1 * | 6/2008 | Kawai et al. | 210/501 |
| 2010/0223803 A1 * | 9/2010 | Karlicek et al. | 34/275 |

\* cited by examiner

--Prior Art--

AIR CONDITIONER INCLUDING VIRUS REMOVAL DEVICE

CROSS-REFERENCE TO RELATED APPLICATION

This application claims priority under 35 U.S.C. §119 from Korean Patent Application No. 10-2010-0108908, filed in the Republic of Korea on Nov. 3, 2010, Korean Patent Application No. 10-2010-0108907, filed in the Republic of Korea on Nov. 3, 2010, Korean Patent Application No. 10-2010-0108905, filed in the Republic of Korea on Nov. 3, 2010, Korean Patent Application No. 10-2010-0108904, filed in the Republic of Korea on Nov. 3, 2010, Korean Patent Application No. 10-2010-0108906, filed in the Republic of Korea on Nov. 3, 2010, Korean Patent Application No. 10-2010-0099092, filed in the Republic of Korea on Oct. 12, 2010, Korean Patent Application No. 10-2010-0099091, filed in the Republic of Korea on Oct. 12, 2010, Korean Patent Application No. 10-2010-0099093, filed in the Republic of Korea on Oct. 12, 2010, Korean Patent Application No. 10-2010-0099094, filed in the Republic of Korea on Oct. 12, 2010, Korean Patent Application No. 10-2010-0099086, filed in the Republic of Korea on Oct. 12, 2010, Korean Patent Application No. 10-2010-0099087, filed in the Republic of Korea on Oct. 12, 2010, and Korean Patent Application No. 10-2010-0099089, filed in the Republic of Korea on Oct. 12, 2010, the subject matters of which are incorporated herein by reference.

BACKGROUND

1. Field

Embodiments may relate to a virus removal device with an ultraviolet light emitting diode (LED).

2. Background

In general, an air conditioner includes a compressor, a condenser, an expansion valve, an evaporator, and the like.

Here, the air conditioner has a circulation structure in which a refrigerant discharged from the compressor is again flowed in the compressor via the condenser, the expansion valve and the evaporator. These components are connected to one another through pipes.

Specifically, the compressor is a device that liquefies a high-temperature and high-pressure gas, and the expansion valve is a device that expands a refrigerant in a vapor state at a low temperature and low pressure so that a heat exchange is easy and controls the degree of expansion of the refrigerant. The evaporator is a device that generates cool air by performing a heat exchange between external air flowed in the device by a fan and the cool refrigerant on a pipe installed in the device itself.

Meanwhile, a split-type air conditioner is composed of an indoor unit and an outdoor unit. An evaporator is provided to the indoor unit, and a compressor, a condenser and an expansion valve are provided to the outdoor unit.

FIG. 1 is an internal configuration view of a general air conditioner. As shown in FIG. 1, the air conditioner includes a main body 10, an evaporator 50, a drain pan 70, a fan 40, a fan duct 60 and the like.

An operation of the air conditioner will be described. When the fan 40 in the fan duct 60 is driven by a motor, air is flowed in the inside of the main body 10 through a suction gate 30 positioned a lower part of the main body 10, and cool air is produced by performing a heat exchange between the air flowed in the inside of the main body 10 and a cool refrigerant in the inside of the evaporator. Condensation water collected in the drain pan 70 is discharged to a drain along a drain hose 80.

Meanwhile, the cool air produced by the heat exchange with the evaporator 50 is again flowed in the fan 40 through a suction hole of the fan duct 60 and then exhausted through an exhaustion hole of the fan duct 60 via the fan 40. The air exhausted through the exhaustion hole of the fan duct 60 is completely exhausted to the outside of the main body 10 through an exhaustion gate 20 positioned at an upper part of the main body 10.

In general, an air cleaner is a device that purifies air by filtering dust or viruses in the air. The air cleaner has a ventilation fan that sucks indoor air into a main body constituting the external appearance of the air cleaner and forcibly ventilates the sucked air to the outside of the air cleaner, and a filter that filters pollutants such as dust or viruses in the air. In the air cleaner, the indoor air is flowed by passing through the filter by a ventilation force generated by the ventilation fan, thereby purifying the indoor air.

One of such air cleaners is an air cleaner that ventilates air in an indoor space by exhausting indoor air to the outside of the indoor space and sucking outdoor air into the indoor space.

Since the air cleaner capable of performing a ventilation operation as described above should perform the exhaustion of the indoor air and the suction of the outdoor air at the same time, a ventilation fan for exhausting indoor air and a ventilation fan for sucking outdoor air are provided to the air cleaner. The air cleaner has a driving motor for driving the two ventilation fans so that the two ventilation fans are positioned at both sides of the driving motor, respectively. Thus, the driving motor rotates the two ventilation fans are rotated, thereby generating a ventilation force.

Accordingly, when the two ventilation fans are rotated under an operation of the driving motor, one ventilation fan exhausts the indoor air to the outside of the indoor space, and the other ventilation fan sucks the outdoor air into the indoor space, thereby ventilating the indoor space.

SUMMARY

Embodiments provide an air conditioner having a virus removal device with an ultraviolet LED, which can effectively remove microbes and viruses bred in an evaporator and a drain pan.

Embodiments also provide an air cleaner having a virus removal device with an ultraviolet LED, which can sterilize a filter for filtering pollutants such as dust or viruses in air sucked into the air cleaner.

One embodiment is a virus removal device with an ultraviolet LED. The virus removal device includes: an operating member; an ultraviolet LED configured to irradiate ultraviolet light onto an object under an operation of the operating member; and a driving means configured to generate a driving force so that the operating member is moved.

Another embodiment is a virus removal device with an ultraviolet LED. The virus removal device includes: an operating member having a reflection body; an ultraviolet LED configured to irradiate ultraviolet light onto an object to be sterilized by reflecting the irradiated light on the reflection body of the operating member; and a driving means configured to generate a driving force so that the operating member is moved.

Further another embodiment is a virus removal device with an ultraviolet LED. The virus removal device includes: a guide member; a moving means guided along the guide member; an ultraviolet LED disposed on the moving means; and a driving means connected to the moving means so that the moving means is moved to left and right.

BRIEF DESCRIPTION OF THE DRAWINGS

Arrangements and embodiments may be described in detail with reference to the following drawings in which like reference numerals refer to like elements and wherein.

DETAILED DESCRIPTION

A thickness or a size of each layer may be magnified, omitted or schematically shown for the purpose of convenience and clearness of description. The size of each component may not necessarily mean its actual size.

It should be understood that when an element is referred to as being 'on' or "under" another element, it may be directly on/under the element, and/or one or more intervening elements may also be present. When an element is referred to as being 'on' or 'under', 'under the element' as well as 'on the element' may be included based on the element.

An embodiment may be described in detail with reference to the accompanying drawings.

Figure 1:
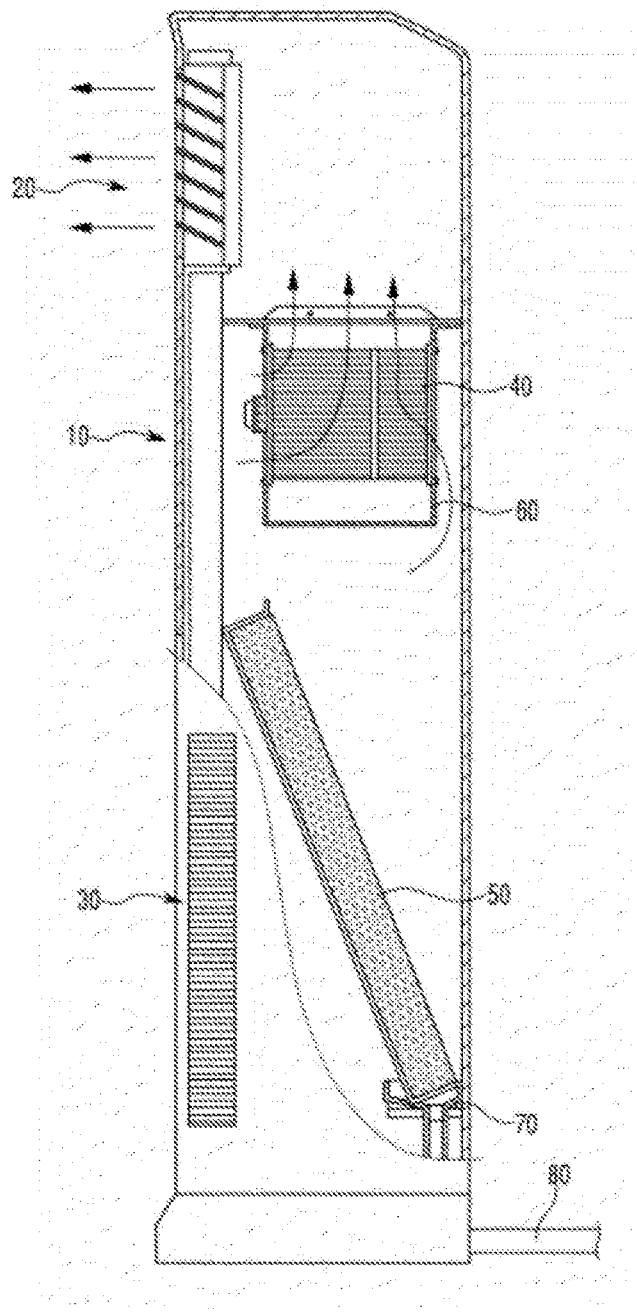
FIG. 1 is an internal configuration view of a general air conditioner.
Figure 2:
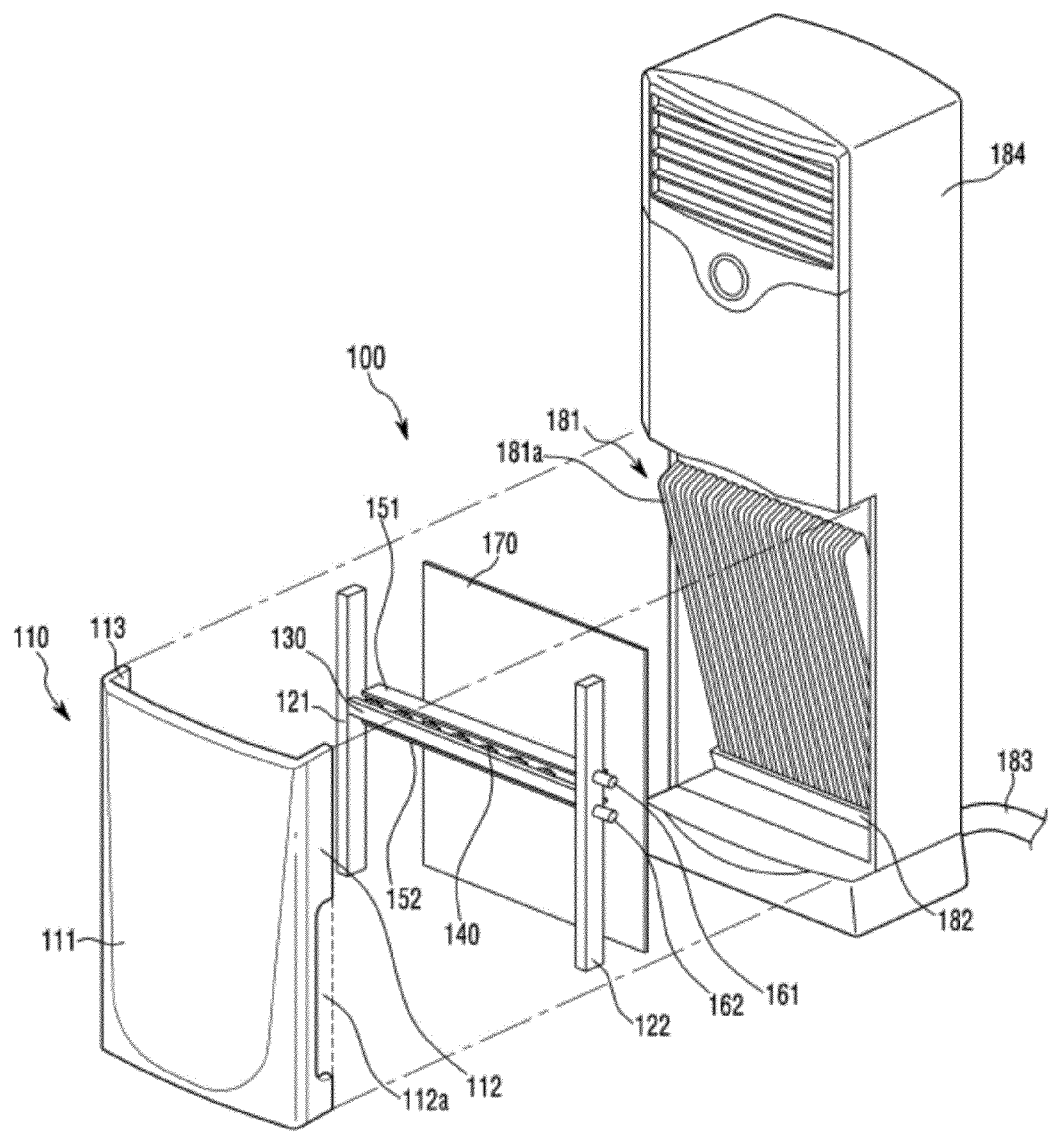
FIG. 2 is an exploded perspective view of an air conditioner to which a virus removal device with an ultraviolet LED is applied according to a first embodiment.
Figure 3:
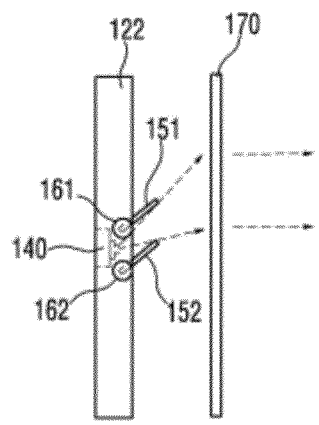
FIG. 3 is a perspective view showing a state where upper and lower plates of FIG. 2 are inclined upward.
Figure 4:
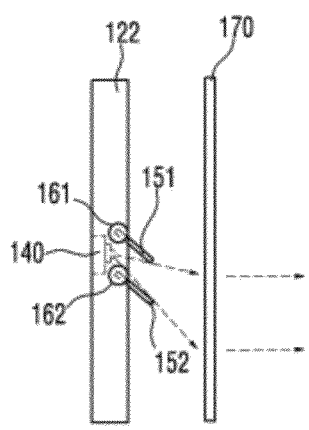
FIG. 4 is a perspective view showing a state where the upper and lower plates of FIG. 2 are inclined downward.

FIG. 2 is an exploded perspective view of an air conditioner to which a virus removal device with an ultraviolet LED is applied according to a first embodiment. FIG. 3 is a perspective view showing a state where upper and lower plates of FIG. 2 are inclined upward. FIG. 4 is a perspective view showing a state where the upper and lower plates of FIG. 2 are inclined downward. Referring to FIG. 2, the air conditioner may include an evaporator 181, a panel 110, a virus removal device 100 and a power control device (not shown). The virus removal device 100 may include vertical members 121 and 122, a horizontal member 130, plates 151 and 152, an ultraviolet LED 140, a heat dissipater (not shown), a diffusion sheet 170 and a driving means.

The evaporator 181 is mounted in the inside of the air conditioner, and has a plurality of pins 181a disposed in parallel to one another. The air conditioner is provided with a main body 184 having a suction gate for sucking air and an exhaustion gate for exhausting the sucked air. A fan rotated to suck the air through the suction gate or exhaust the air through the exhaustion gate is provided to the inside of the main body 184. The evaporator 181 generates cool air by performing a heat exchange with the air flowed in the main body 184 through the suction gate under an operation of the fan.

The panel 110 includes a front part 111 and guide parts 112 and 113 extended in a vertical direction from the front part 111. Each of the guide parts 112 and 113 has an opening 112a through which the air is sucked from both sides of the front part 111. The panel 110 covers the evaporator 181. The openings 112a at both the sides of the front part 111 have the same shape as each other, and the guide parts 112 and 113 at both the sides of the front part 111 have the same shape as each other. When viewing the panel 110 from the top, the panel 110 has a "=" shape that is a plane shape of which one and the other ends are bent to one side of the panel 110. The openings 112a have shapes in which grooves are formed in the respective guide parts 112 and 113, and are formed in the same direction as the length direction of the pins 181a of the evaporator 181.

The first and second vertical members 121 and 122 are disposed in parallel to each other in the inside between the pair of the guide parts 112 and 113, and have holes. First and second holes are formed in each of the first and second vertical members 121 and 122. The first holes respectively formed in the first and second vertical members 121 and 122 are disposed opposite to each other so that protruding parts at one and the other ends of the horizontal member 130 are inserted into the respective first holes. The second holes respectively formed in the first and second vertical members 121 and 122 are disposed opposite to each other so that protruding parts at one and the other ends of the plates 151 and 152 are inserted into the respective second holes.

One side of the horizontal member 130 is disposed at the first vertical member 121, and the other side of the horizontal member 130 is disposed at the second vertical member 122. The protruding parts at the one and the other ends of the horizontal member 130 are inserted into the first holes formed in the first and second vertical members 121 and 122, respectively.

The plate is provided with an upper plate 151 disposed above the horizontal member 130 and a lower plate 152 disposed below the horizontal member 130. Each of the plates 151 and 152 has circular protruding parts respectively formed at one and the other end thereof, and the protruding parts are inserted into the second holes formed in the first and second vertical members 121 and 122, respectively. The upper and lower plates 151 and 152 are rotated to a predetermined angle in the state where they are disposed in parallel to each other.

That is, the upper and lower plates 151 and 152 are rotated in the length direction of the pins within the predetermined angle in the state where they are disposed in parallel to each other. The upper and lower plates 151 and 152 are rotated upward and downward in the state where the protruding parts are inserted into the respective second holes. The radius of the protruding part is formed smaller than or identical to that of the second hole, and thus the plates 151 and 152 are rotated in the state where the protruding part comes in contact with the second hole. The plates 151 and 152 are rotated so that the angles at which the plates 151 and 152 are rotated respectively upward and downward in the state where the direction of surfaces of the plates 151 and 152 is a vertical direction are identical to each other.

Unlike the embodiment, the upper and lower plates 151 and 152 may be integrally formed to be integrally driven by being respectively inserted into holes formed in both the vertical members 121 and 122. In this case, the number of holes formed in each of the vertical members 121 and 122 is one. Alternately, the upper and lower plates 151 and 152 may be separately formed to separately move by being respectively inserted into holes formed in both the vertical members 121 and 122. In this case, the number of holes formed in each of the vertical members 121 and 122 is two. When the upper and lower plates 151 and 152 are separately formed and the horizontal member 130 is also inserted together with the upper and lower plates 151 and 152 into the vertical members 121 and 122, three holes may be formed in each of the vertical members 121 and 122.

A plurality of ultraviolet LEDs 140 may be disposed toward an object to be sterilized, i.e., the evaporator 181, at the same interval on one side of the horizontal member 130. The ultraviolet LEDs 140 are disposed in a direction vertical to the length direction of the plurality of pins 181a of the evaporator 181 so as to irradiate light onto the evaporator 181. That is, the ultraviolet LEDs 140 are disposed in the direction vertical to the length direction of the pins 181a so as to irradiate light onto the evaporator 181 through the plates 151 and 152. Specifically, the ultraviolet LEDs 140 are disposed on an upper surface of a base part such as a PCB, so as to remove microbes or viruses bred in the evaporator 181 and a drain pan 182 for collecting condensation water flowing from surfaces of the evaporator 181 at a lower part of the evaporator 181. The position at which the light generated from the ultraviolet LEDs 140 reaches the evaporator 181 is changed in the length direction of the pins 181a depending on time.

The heat dissipater (not shown) may be disposed to dissipate heat generated due to the light emission of the ultraviolet LED 140. The heat dissipater is disposed adjacent to the base part disposed beneath the ultraviolet LED 140 below the base part, so as to dissipate the heat generated from the ultraviolet LED 140. The heat dissipater may be formed of a carbon nanotube (CNT) composite material. A carbon nanotube is a kind of carbon allotrope made of carbon, and has a tube shape that cylindrically winds a graphite sheet obtained by bonding one carbon atom to other carbon atoms in a hexagonal honeycomb. The diameter of the carbon nanotube is about 1 to 100 nm. The carbon nanotube has characteristics of high thermal quality, electric conductivity and high solidity, and thus can be used for the heat dissipater of the ultraviolet LED 140.

The diffusion sheet 170 diffuses light emitted from the ultraviolet LED 140 toward the evaporator 181. The diffusion sheet 170 is disposed between the base part and the evaporator 181, so that ultraviolet light, as shown in FIGS. 3 and 4, can be uniformly thrown on the evaporator 181 and the drain pan 182 as compared with a case where the diffusion sheet 170 is not disposed. Accordingly, it is possible to remove even microbes and viruses located at corners of the evaporator 181 and the drain pan 182.

The driving means generates a driving force for rotating the plates 151 and 152. The driving means includes first and second motors 161 and 162 respectively connected to one sides of the upper and lower plates 151 and 152. When the first and second motors 161 and 162 rotate in a positive direction, the plates 151 and 152 are rotated in one direction. When the first and second motors 161 and 162 rotate in a reverse direction, the plates 151 and 152 are rotated in the opposite direction to the one direction. Specifically, the first and second motors 161 and 162 are connected to the respective plates 151 and 152 by passing through the vertical members 121 and 122. The first and second motors 161 and 162 rotate the plates 151 and 152 to be rotated in one or the other direction. FIG. 3 shows a state where the plates 151 and 152 are rotated upward. FIG. 4 shows a state where the plates 151 and 152 are rotated downward. When the angle at which the plates 151 and 152 are rotated upward is identical to that at which the plates 151 and 152 are rotated downward at the middle position of the evaporator 181, light can be equally irradiated onto the evaporator 181 from the ultraviolet LED 140.

The power control device is turned off when a first setup time elapses after the ultraviolet LED 140 is turned on. The power control device is turned on when a second setup time elapses after the ultraviolet LED 140 is turned off. The power control device may repeatedly perform the turn-on and turn-off operations. The power control device will be described in detail with reference to FIG. 5.

Meanwhile, an operation of the air conditioner having the virus removal device according to the first embodiment will be described. When air is flowed into the inside of the main body 184 through the suction gate together with the operation of the fan, the air is cooled down through a heat exchange between the air and the evaporator 181. Condensation water flows down from surfaces of the evaporator 181. Then, the condensation water is collected into the drain pan 181 positioned at the lower part of the evaporator 181 so as to be discharged to a drain along a hose 183.

In the operation state described above, the evaporator 181 and the drain pan 182 always maintains a wet state and a temperature suitable for the microbes and viruses to be bred. Therefore, when cool air is supplied to an indoor space through the exhaustion gate due to the continuous operation of the fan, the microbes and viruses bred in the evaporator 181 and the drain pan 182 may be exhausted together with the cool air so as to threaten users' health.

In this situation, the virus removal device 100 can effectively remove the microbes and viruses bred in the evaporator 181 and the drain pan 182 using the ultraviolet light emitted from the ultraviolet LED 140 in the length direction of the evaporator 181, which is vertical to the drain pan 182.

Figure 5:
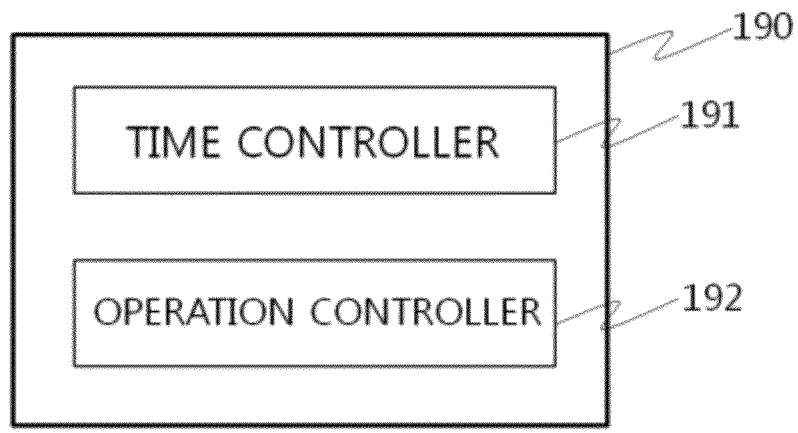
FIG. 5 is a block diagram of a power control device of the air conditioner to which a virus removal device with an ultraviolet LED is applied according to first to eleventh embodiments.

FIG. 5 is a block diagram of a power control device of the air conditioner to which a virus removal device with an ultraviolet LED is applied according to first to eleventh. Referring to FIG. 5, the power control device 190 includes a time controller 191 and an operation controller 129. FIG. 5 will be described together with FIGS. 2 to 4.

In the operation of the ultraviolet LED 140 of FIGS. 2 to 4, the microbes and viruses bred in the evaporator 181 and the drain pan 182 can be removed by always turning on the ultraviolet LED 140, but the ultraviolet LED 140 may be turned on only for a certain period of time for the purpose of power reduction and energy saving.

That is, the ultraviolet LED 140 may repeatedly perform an operation of being turned off when a first setup time elapses after the ultraviolet LED 140 is turned on and being turned on when a second setup time elapses after the ultraviolet LED 140 is turned off. For example, the ultraviolet LED 140 may repeatedly perform an operation of being turned off when 30 minutes elapses after the ultraviolet LED 140 is turned on and being turned on when an hour elapses after the ultraviolet LED 140 is turned off. The time in the control of the turn-on/turn-off of the ultraviolet LED 140 is not limited thereto and may be variously set up.

As such, the power control device 190 may be additionally provided to the base part so as to control turn-on and turn-off operations of the ultraviolet LED 140. The power control device 190 may be connected to the ultraviolet LED 140 through the base part. The power control device 190 includes a time controller 191 and an operation controller 192.

The time controller 191 counts a time and determines whether or not the counted time correspond to a setup time. The count time unit 191 does not generate an operation control signal when the counted time does not correspond to the setup time, and generates the operation control signal only when the counted time corresponds to the setup time. Then, the count time unit 191 transmits the operation control signal to the operation controller 192. That is, when the counted time corresponds to the setup time, the time controller 191 continuously generates the operation control signal and transmits the operation control signal to the operation controller 192. When the counted time does not correspond to the setup time, the time controller 191 does not generate the operation control signal.

When the counted time corresponds to the setup time, the operation controller 192 receives the operation control signal from the time controller 191 and operates the ultraviolet LED 140. That is, when the counted time corresponds to the setup time, the operation controller 192 continuously receives the operation control signal from the time controller 191 and operates the ultraviolet LED 140. When the counted time elapses and does not correspond to the setup time, the operation controller 192 does not receive the operation control signal, and therefore cannot operate the ultraviolet LED 140.

Figure 6:
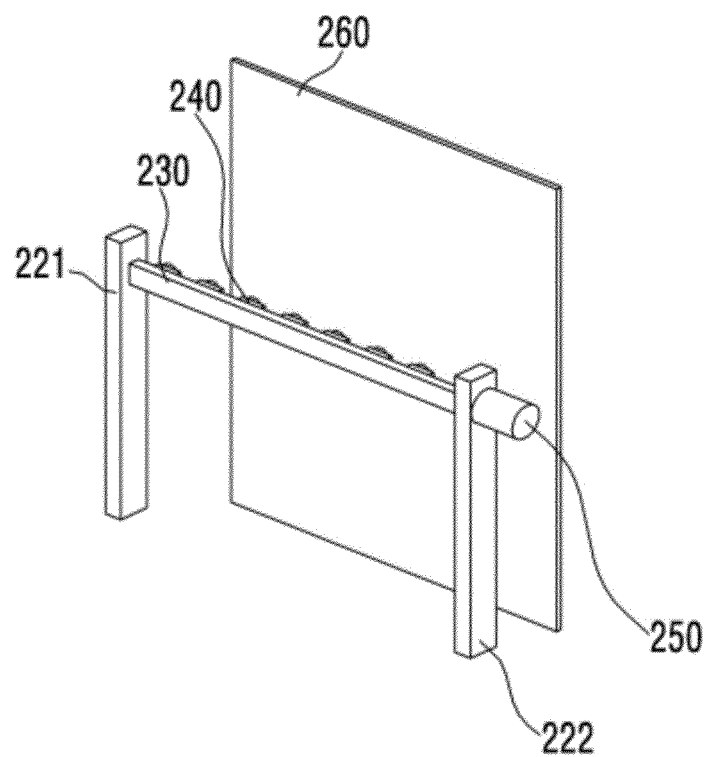
FIG. 6 is a perspective view showing a virus removal device with an ultraviolet LED according to a second embodiment.
Figure 7:
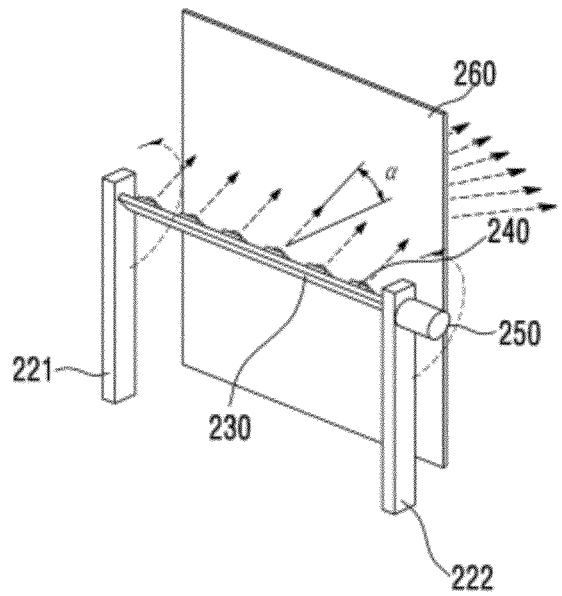
FIG. 7 is a perspective view showing a state where a rotary member of FIG. 6 is rotated upward.
Figure 8:
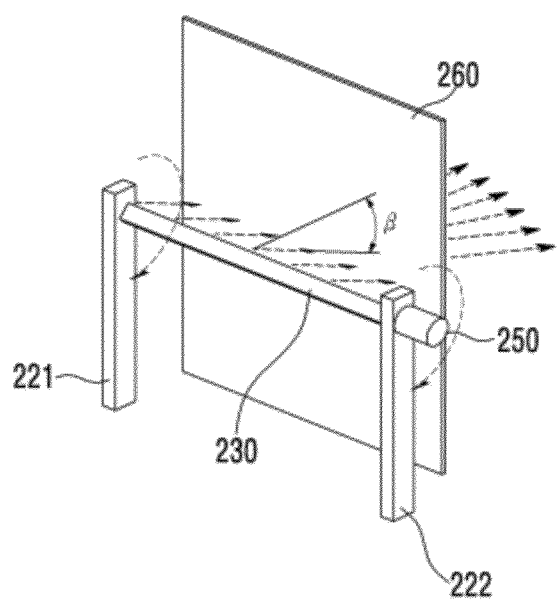
FIG. 8 is a perspective view showing a state where the rotary member of FIG. 6 is rotated downward.

FIG. 6 is a perspective view showing a virus removal device with an ultraviolet LED according to a second embodiment. FIG. 7 is a perspective view showing a state where a rotary member of FIG. 6 is rotated upward. FIG. 8 is a perspective view showing a state where the rotary member of FIG. 6 is rotated downward. Referring to FIGS. 2 and 6, the virus removal device may include a first vertical member 221, a second vertical member 222, a rotary member 230, a base part (not shown), an ultraviolet LED 240, a heat dissipater (not shown), a diffusion sheet 260 and a driving means.

The first and second vertical members 221 and 222 are disposed in parallel to each other, and have holes. The holes respectively formed in the first and second vertical members 121 and 122 are disposed opposite to each other so that protruding parts at one and the other ends of the rotary member 230 are inserted into the holes, respectively.

The circular protruding part formed at the one end of the rotary member 230 is inserted into the hole of the first vertical member 221, and the circular protruding part formed at the other end of the rotary member 230 is inserted into the hole of the second vertical member 222, so that the rotary member 230 is rotated to a predetermined angle. The rotary member 230 is rotated upward and downward in the state where the protruding parts are inserted into the respective holes of the first and second vertical members 221 and 222. The radius of the protruding part is formed smaller than or identical to that of the hole, so that the rotary member 230 is rotated in the state where the protruding part and the hole come in contact with each other. The rotary member 230 is rotated so that the angles at which the rotary member 230 is rotated respectively upward and downward are identical to each other.

A plurality of ultraviolet LEDs 240 may be disposed toward an object to be sterilized at the same interval on one side of the rotary member 230. For example, in the air conditioner shown in FIG. 2, the ultraviolet LEDs 240 are disposed in a direction vertical to the length direction of the plurality of pins 181a of the evaporator 181 so as to irradiate light onto the evaporator 181. Specifically, the ultraviolet LEDs 240 are disposed on an upper surface of a base part such as a PCB, so as to remove microbes or viruses bred in the evaporator 181 and the drain pan 182 for collecting condensation water flowing from surfaces of the evaporator 181 at a lower part of the evaporator 181. The position at which the light generated from the ultraviolet LEDs 240 reaches the evaporator 181 is changed in the length direction of the pins 181a depending on time.

The heat dissipater (not shown) may be disposed to dissipate heat generated due to the light emission of the ultraviolet LED 240. The heat dissipater is disposed adjacent to the base part disposed beneath the ultraviolet LED 240 below the base part, so as to dissipate the heat generated from the ultraviolet LED 240. The heat dissipater may be formed of a carbon nanotube (CNT) composite material.

The diffusion sheet 260 diffuses light emitted from the ultraviolet LED 240 toward the object to be sterilized. The diffusion sheet 260 is disposed between the base part and the object to be sterilized, so that ultraviolet light can be uniformly thrown on the object to be sterilized as compared with a case where the diffusion sheet 260 is not disposed. For example, in the air conditioner shown in FIG. 2, the ultraviolet light can be uniformly thrown on the evaporator 181 and the drain pan 182. Accordingly, it is possible to remove even microbes and viruses located at corners of the evaporator 181 and the drain pan 182.

The driving means generates a driving force for rotating the rotary member 230. The driving means includes a motor 250 connected to one side of the rotary member 230. When the motor 250 rotates in a positive direction, the rotary member 230 is rotated in one direction. When the motor 250 rotates in a reverse direction, the rotary member 230 is rotated in the opposite direction to the one direction. Specifically, the motor 250 is connected to the rotary member 230 by passing through the vertical members 221 and 222. The motor 250 rotates the rotary member 230 to be rotated in one or the other direction. FIG. 7 shows a state where the rotary member 230 is rotated upward. In FIG. 7, a is an angle at which the rotary member 230 is rotated upward. FIG. 8 shows a state where the rotary member 230 is rotated downward. In FIG. 8, 13 is an angle at which the rotary member 230 is rotated downward. In the air conditioner shown in FIG. 2, the angles α and β are identical to each other at the middle position of the evaporator 181, so that light can be equally irradiated onto the evaporator 181 from the ultraviolet LED 240.

Meanwhile, the operation of the air conditioner according to the second embodiment is the same as described in FIG. 2.

Figure 9:
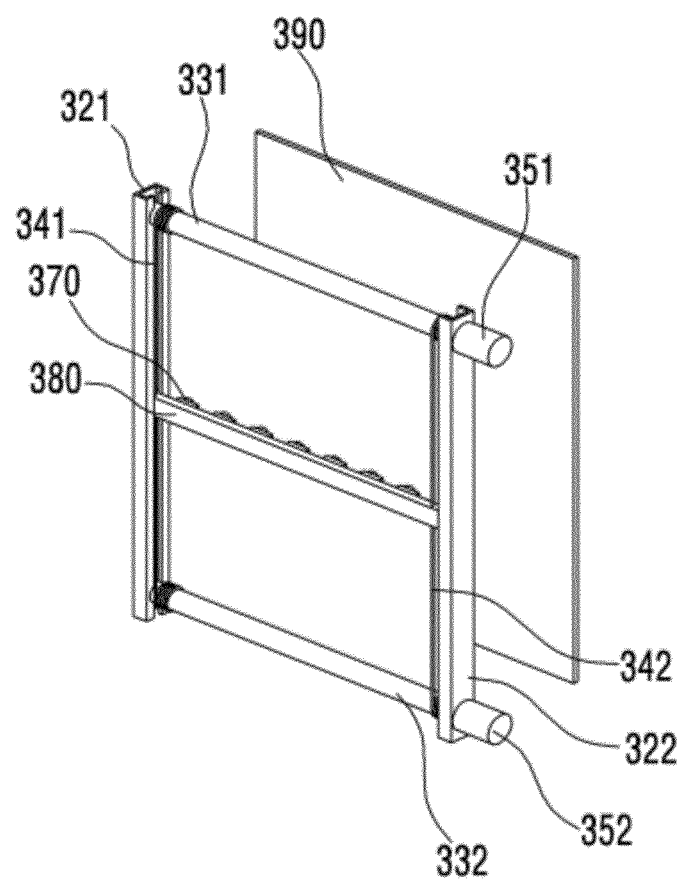
FIG. 9 is a perspective view showing a virus removal device with an ultraviolet LED according to a third embodiment.
Figure 10:
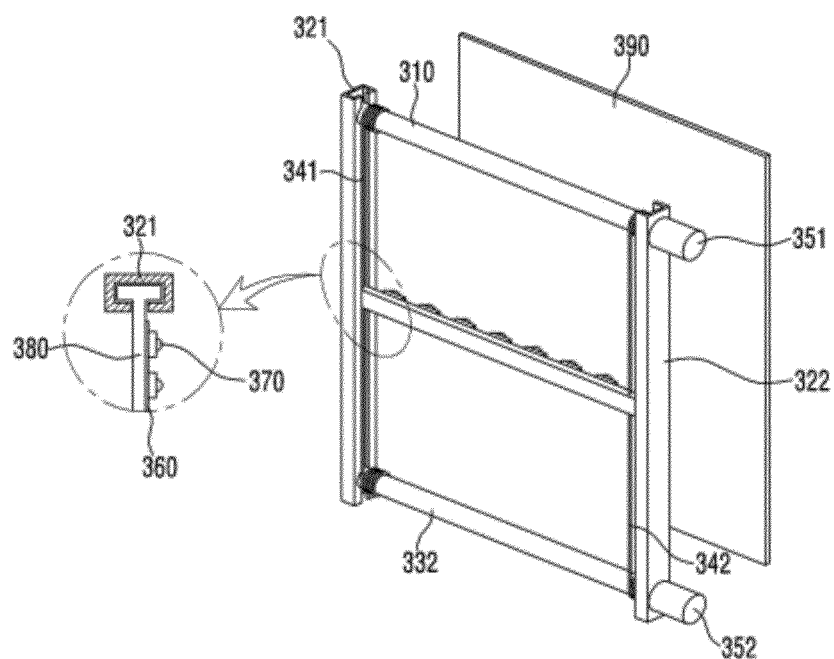
FIG. 10 is a perspective view showing a structure in which a moving member of FIG. 9 is mounted in a guide groove.
Figure 11:
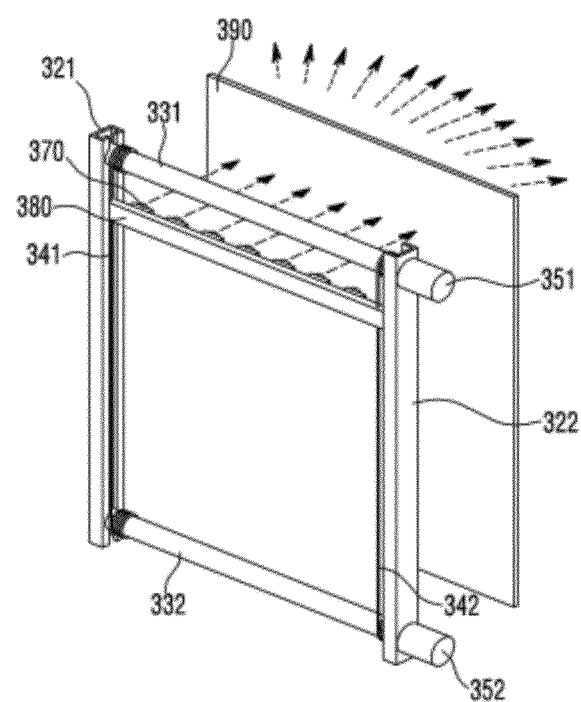
FIG. 11 is a perspective view showing a state where the moving member of FIG. 9 is moved to an upper part.
Figure 12:
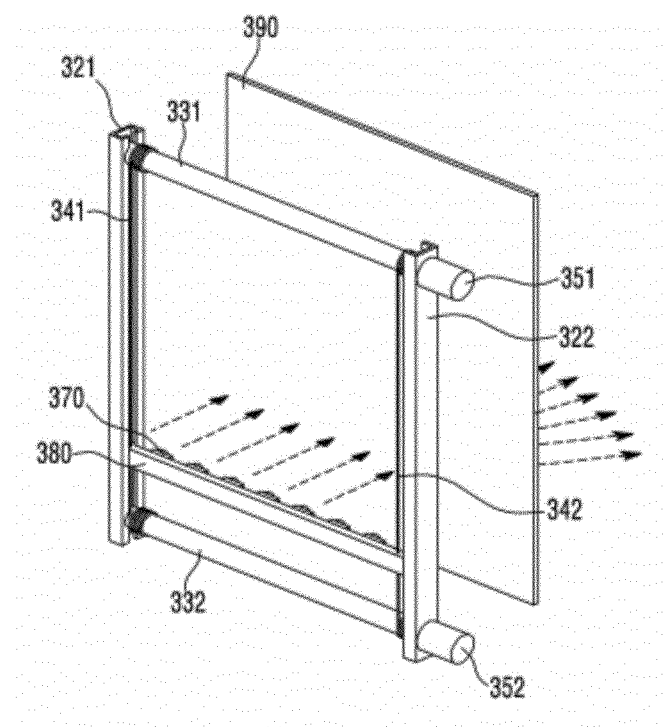
FIG. 12 is a perspective view showing a state where the moving member of FIG. 9 is moved to a lower part.

FIG. 9 is a perspective view showing a virus removal device with an ultraviolet LED according to a third embodiment. FIG. 10 is a perspective view showing a structure in which a moving member of FIG. 9 is mounted in a guide groove. FIG. 11 is a perspective view showing a state where the moving member of FIG. 9 is moved to an upper part. FIG. 12 is a perspective view showing a state where the moving member of FIG. 9 is moved to a lower part. Referring to FIGS. 2 and 9, the virus removal device may include guide members 321 and 322, a moving member 380, a base part 360, an ultraviolet LED 370, a heat dissipater (not shown), a diffusion sheet 390 and a driving means.

The guide members 321 and 322 are disposed in parallel to each other, and have guide grooves. The guide grooves respectively formed at the guide members 321 and 322 are disposed opposite to each other so that one and the other ends of the moving member 380 are inserted into the guide grooves, respectively.

The moving member 380 is mounted in the guide grooves of the guide members 321 and 322, so as to move to top and bottom in the length direction of the guide members 321 and 322. The one end of the moving member 380 is mounted in one guide groove, and the other end of the moving member 380 is mounted in the other guide groove. The moving member 380 is moved to top and bottom in the state where the one and the other end of the moving member 380 come in contact with inner surfaces of the guide grooves, respectively.

A plurality of ultraviolet LEDs 370 may be disposed toward an object to be sterilized at the same interval on one side of the moving member 380. Referring to the air conditioner shown in FIG. 2, the ultraviolet LEDs 370 are disposed in a direction vertical to the length direction of the plurality of pins 181a of the evaporator 181 so as to irradiate light onto the evaporator 181. Specifically, the ultraviolet LEDs 370 are disposed on an upper surface of the base part 360 such as a PCB, so as to remove microbes or viruses bred in the evaporator 181 and the drain pan 182 for collecting condensation water flowing from surfaces of the evaporator 181 at a lower part of the evaporator 181. The position at which the light generated from the ultraviolet LEDs 370 reaches the evaporator 181 is changed in the length direction of the pins 181a depending on time.

The heat dissipater (not shown) may be disposed to dissipate heat generated due to the light emission of the ultraviolet LED 370. The heat dissipater is disposed adjacent to the base part 360 disposed beneath the ultraviolet LED 370 below the base part, so as to dissipate the heat generated from the ultraviolet LED 370. The heat dissipater may be formed of a carbon nanotube (CNT) composite material.

The diffusion sheet 390 diffuses light emitted from the ultraviolet LED 370 toward the object to be sterilized. The diffusion sheet 390 is disposed between the base part and the object to be sterilized, so that ultraviolet light can be uniformly thrown on the object to be sterilized as compared with a case where the diffusion sheet 390 is not disposed. Referring to the air conditioner shown in FIG. 2, the ultraviolet light can be uniformly thrown on the evaporator 181 and the drain pan 182 as shown in FIGS. 2, 11 and 12. Accordingly, it is possible to remove even microbes and viruses located at corners of the evaporator 181 and the drain pan 182.

The driving means generates a driving force to allow the moving member 380 to move to top and bottom. The driving means includes first and second motors 351 and 352 respectively connected to one sides of upper and lower rotary shafts 331 and 332a. When the first and second motors 351 and 352 rotate in a positive direction, the moving member 380 is moved to an upper part of the driving means. When the first and second motors 351 and 352 rotate in a reverse direction, the moving member 380 is moved to a lower part of the driving means. Specifically, the first and second motors 351 and 352 are connected to the respective rotary shafts 331 and 332 by passing through the guide members 321 and 322. The first and second motors 351 and 352 rotate the rotary shafts 331 and 332 to be rotated in one or the other direction. Since the moving member 380 is wound with the upper and lower rotary shafts 331 and 332 using a wire, the moving member 380 can be moved to top and bottom between the upper and lower rotary shafts 331 and 332 by the driving force of the first and second motors 351 and 352. FIG. 11 shows a state where the moving member 380 is moved to an upper part of the driving means. FIG. 12 shows a state where the moving member 380 is moved to a lower part of the driving means.

Figure 13:
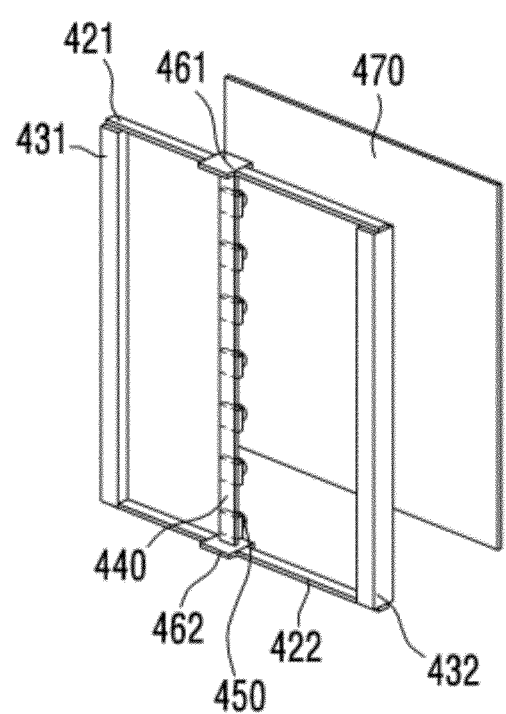
FIG. 13 is a perspective view showing a virus removal device with an ultraviolet LED according to a fourth embodiment.
Figure 14:
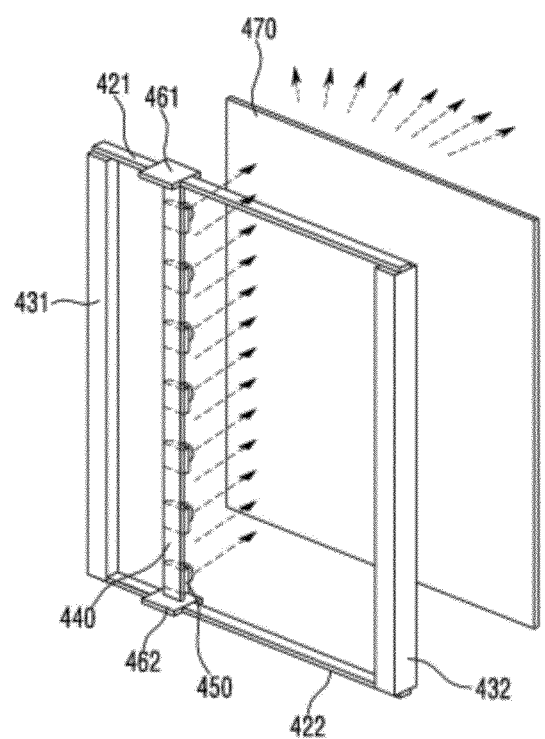
FIG. 14 is a perspective view showing a state where a moving member of FIG. 13 is moved to a left side.
Figure 15:
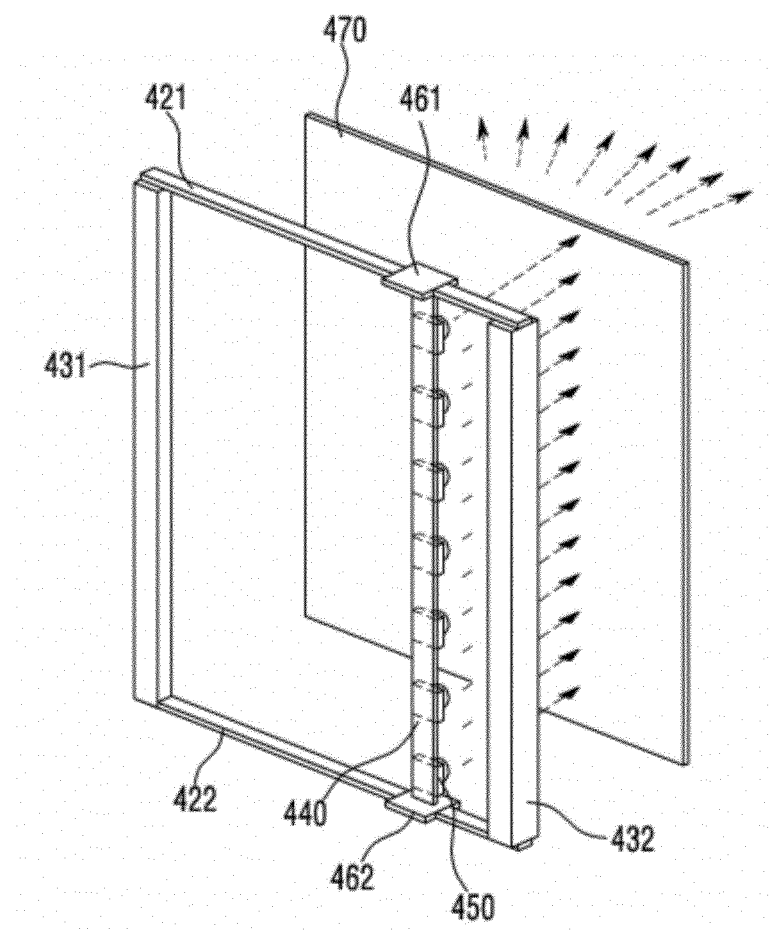
FIG. 15 is a perspective view showing a state where the moving member of FIG. 13 is moved to a right side.

FIG. 13 is a perspective view showing a virus removal device with an ultraviolet LED according to a fourth embodiment. FIG. 14 is a perspective view showing a state where a moving member of FIG. 13 is moved to a left side. FIG. 15 is a perspective view showing a state where the moving member of FIG. 13 is moved to a right side. Referring to FIGS. 2 and 13, the virus removal device may include guide members 421 and 422, vertical members 431 and 432, a moving member 440, a base member (not shown), a heat dissipater (not shown), an ultraviolet LED 450, a diffusion sheet 470 and a driving means.

The guide member 421 is disposed at one sides of the vertical members 431 and 432, and the guide member 422 is disposed at the other sides of the vertical members 431 and 432. The guide members 421 and 422 are disposed in parallel with each other, and have guide rails. The guide rails formed at the pair of the guide members 421 and 422 provide a moving path of the driving means.

The moving member 440 is moved in the length direction of the guide members 421 and 422. That is, the moving member 440 is moved to left and right in a direction vertical to the length direction of an object to be sterilized. When comparing FIGS. 14 and 15, FIG. 14 shows a state where light is irradiated when the moving member 440 is positioned at a left side, and FIG. 15 shows a state where light is irradiated when the moving member 440 is positioned at a right side.

A plurality of ultraviolet LEDs 450 may be disposed along the length direction of the moving member 440 toward an object to be sterilized at the same interval on one side of the moving member 440. The ultraviolet LEDs 450 are disposed in the length direction of the moving member 440 so as to irradiate light onto the object to be sterilized. Specifically, referring to the air conditioner shown in FIG. 2, the ultraviolet LEDs 450 are disposed on an upper surface of the base part such as a PCB. The plurality of ultraviolet LEDs 450 are disposed along the vertical length direction of the evaporator 181 based on the drain pan 182 so as to remove microbes or viruses bred in the evaporator 181 and the drain pan 182 for collecting condensation water flowing from surfaces of the evaporator 181 at a lower part of the evaporator 181. The position at which the light generated from the ultraviolet LEDs 450 reaches the evaporator 181 is changed in a direction vertical to the length direction of the pins 181a depending on time.

The heat dissipater (not shown) may be disposed to dissipate heat generated due to the light emission of the ultraviolet LED 450. The heat dissipater is disposed adjacent to the base part disposed beneath the ultraviolet LED 450 below the base part, so as to dissipate the heat generated from the ultraviolet LED 450. The heat dissipater may be formed of a carbon nanotube (CNT) composite material.

The diffusion sheet 470 diffuses light emitted from the ultraviolet LED 450 toward the object to be sterilized. The diffusion sheet 470 is disposed between the base part and the object to be sterilized, so that ultraviolet light can be uniformly thrown on the object to be sterilized as compared with a case where the diffusion sheet 470 is not disposed. Referring to the air conditioner shown in FIG. 2, the ultraviolet light can be uniformly thrown on the evaporator 181 and the drain pan 182 as shown in FIGS. 2, 14 and 15. Accordingly, it is possible to remove even microbes and viruses located at corners of the evaporator 181 and the drain pan 182.

The driving means is connected to the moving member 440, and generates a driving force while moving along the length direction of the guide members 421 and 422, so that the moving member 440 is moved to left and right. The driving means includes a first motor 461 and a second motor 462. The moving member 440 is moved to left and right in the length direction of the guide members 421 and 422 by the driving force of the first and second motors 461 and 462. Specifically, the first and second motors 461 and 462 are connected to the moving member, and allow the moving member 440 to move to left and right along the guide rails. It will be apparent that the first and second motors 461 and 462 may be formed in a single body so as to allow the moving member 440 to move to left and right.

Figure 16:
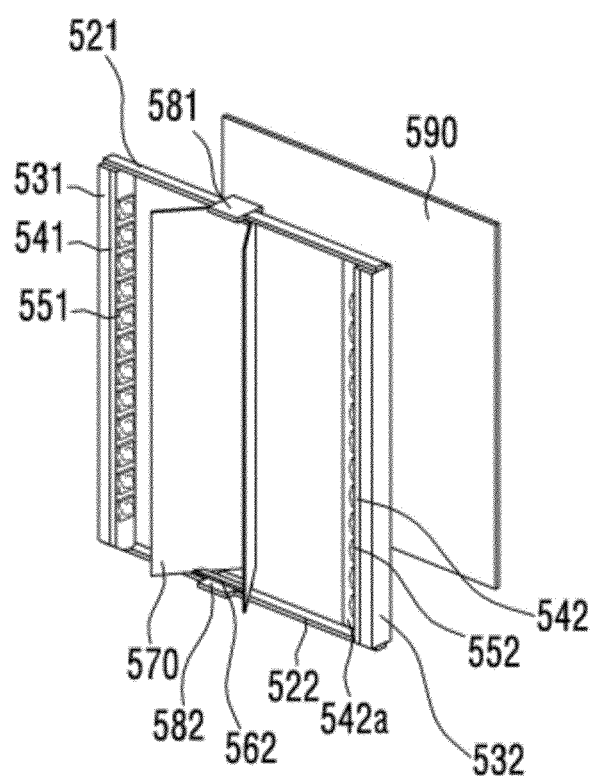
FIG. 16 is a perspective view showing a virus removal device with an ultraviolet LED according to a fifth embodiment.
Figure 17:
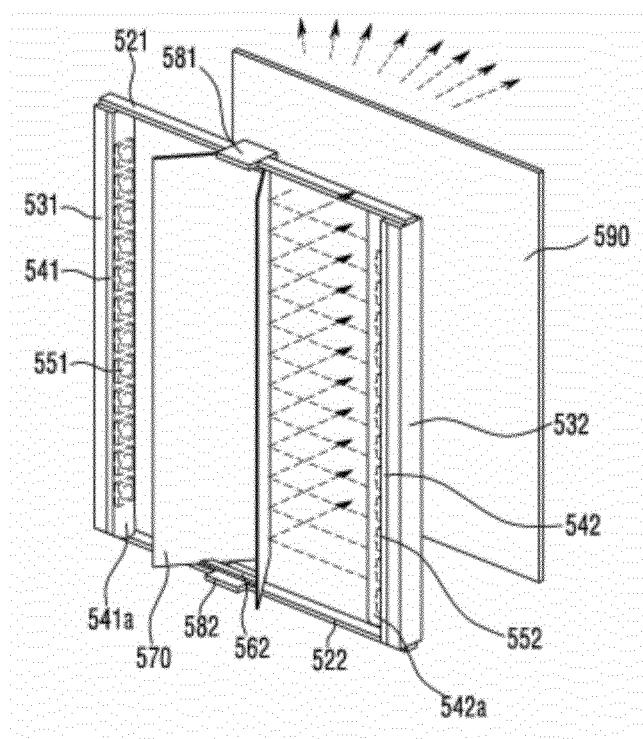
FIG. 17 is a perspective view showing a state where a reflector of FIG. 16 is moved to the left side.
Figure 18:
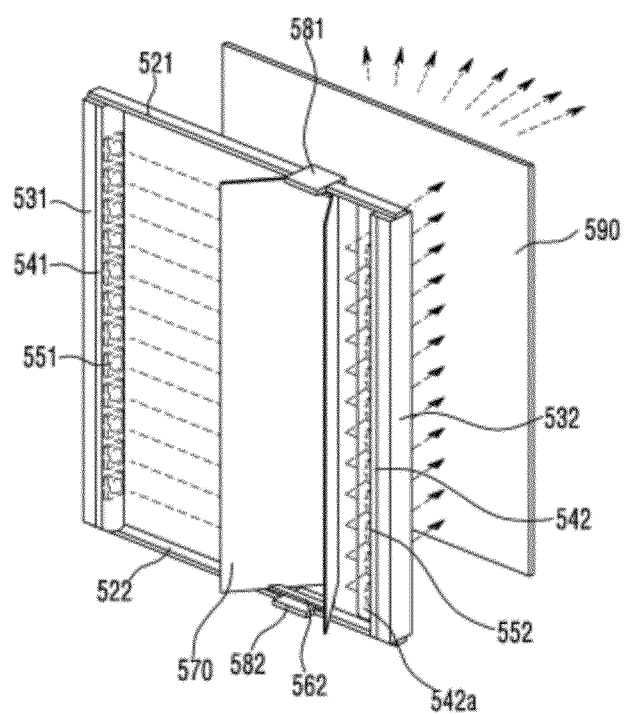
FIG. 18 is a perspective view showing a state where the reflector of FIG. 16 is moved to the right side.

FIG. 16 is a perspective view showing a virus removal device with an ultraviolet LED according to a fifth embodiment. FIG. 17 is a perspective view showing a state where a reflector of FIG. 16 is moved to the left side. FIG. 18 is a perspective view showing a state where the reflector of FIG. 16 is moved to the right side. Referring to FIGS. 2 and 16, the virus removal device may include guide members 521 and 522, vertical members 531 and 532, a reflector 570, base parts 541 and 542, heat dissipaters (not shown), ultraviolet LEDs 551 and 552, a diffusion sheet 590 and a driving means.

The guide members 521 and 522 are disposed in parallel to each other, and have guide rails. The guide rails formed at the pair of the guide members 521 and 522 provide moving paths of first and second motors 581 and 582, respectively.

The reflector 570 is moved to left and right in the length direction of the guide members 521 and 522. That is, the reflector 570 is moved to left and right in a direction vertical to the length direction of an object to be sterilized. Referring to FIGS. 17 and 18, FIG. 17 shows a state where light is irradiated when the reflector 570 is positioned at a left side, and FIG. 18 shows a state where light is irradiated when the reflector 570 is positioned at a right side. The reflector 570 is disposed in the opposite direction to the object to be sterilized based on the positions at which the guide members 521 and 522 are disposed. The reflector 570 includes two reflection surfaces of which one sides come in contact with each other. The angles of the two reflection surfaces coated with aluminum, made with respect to the length direction of the guide members 521 and 522 may be identical to each other. The reflection surfaces may be disposed so that the areas in which light emitted from the ultraviolet LEDs 551 and 552 reach the respective reflection surfaces are identical to each other.

A plurality of ultraviolet LEDs 551 and a plurality of ultraviolet LEDs 552 may be disposed along the length direction of the vertical members 531 and 532 at the same interval. The ultraviolet LEDs 551 and 552 are disposed in the length direction of the reflector 570 so as to irradiate light reflected by the reflector 570 onto the object to be sterilized. Specifically, referring to the air conditioner shown in FIG. 2, the ultraviolet LEDs 551 and 552 are disposed on upper surfaces of the base parts 541 and 542 such as PCBs, respectively. The ultraviolet LEDs 551 and 552 are disposed along the vertical length direction of the evaporator 181 based on the drain pan 182 so as to remove microbes or viruses bred in the evaporator 181 and the drain pan 182 for collecting condensation water flowing from surfaces of the evaporator 181 at a lower part of the evaporator 181. The position at which the light generated from the ultraviolet LEDs 551 and 552 reaches the evaporator 181 is changed in a direction vertical to the length direction of the pins 181a depending on time. The ultraviolet LEDs 551 and 552 are respectively covered with lenses 541a and 542a so that light emitted from the ultraviolet LEDs 551 and 552 is gathered to the reflector 570. Thus, the gathered light can be irradiated toward the evaporator 181.

The heat dissipaters (not shown) may be disposed to dissipate heat generated due to the light emission of the ultraviolet LEDs 551 and 552. The heat dissipaters are respectively disposed adjacent to the base parts 541 and 542 disposed beneath the ultraviolet LEDs 551 and 552 below the base parts 541 and 542, so as to dissipate the heat generated from the ultraviolet LEDs 551 and 552. The heat dissipater may be formed of a carbon nanotube (CNT) composite material.

The diffusion sheet 590 diffuses light reflected from reflector 570 toward the object to be sterilized. The diffusion sheet 590 is disposed between the base parts 541 and 542 and the object to be sterilized, so that ultraviolet light can be uniformly thrown on the object to be sterilized as compared with a case where the diffusion sheet 570 is not disposed. Referring to the air conditioner shown in FIG. 2, the ultraviolet light can be uniformly thrown on the evaporator 181 and the drain pan 182 as shown in FIGS. 2, 17 and 18. Accordingly, it is possible to remove even microbes and viruses located at corners of the evaporator 181 and the drain pan 182.

The driving means is connected to the reflector 570, and generates a driving force while moving along the length direction of the guide members 521 and 522, so that the reflector 570 is moved to left and right. The driving means includes the first and second motors 581 and 582 respectively moved along the length directions of the guide members 521 and 522. The reflector 570 is moved to left and right in the length direction of the guide members 521 and 522 by the driving force of the first and second motors 581 and 582. Specifically, the first and second motors 581 and 582 allow the reflector 570 connected through a connection member 562 (a connection member connected to the first motor 581 is not seen) to move to left and right along the guide members 521 and 522.

Figure 19:
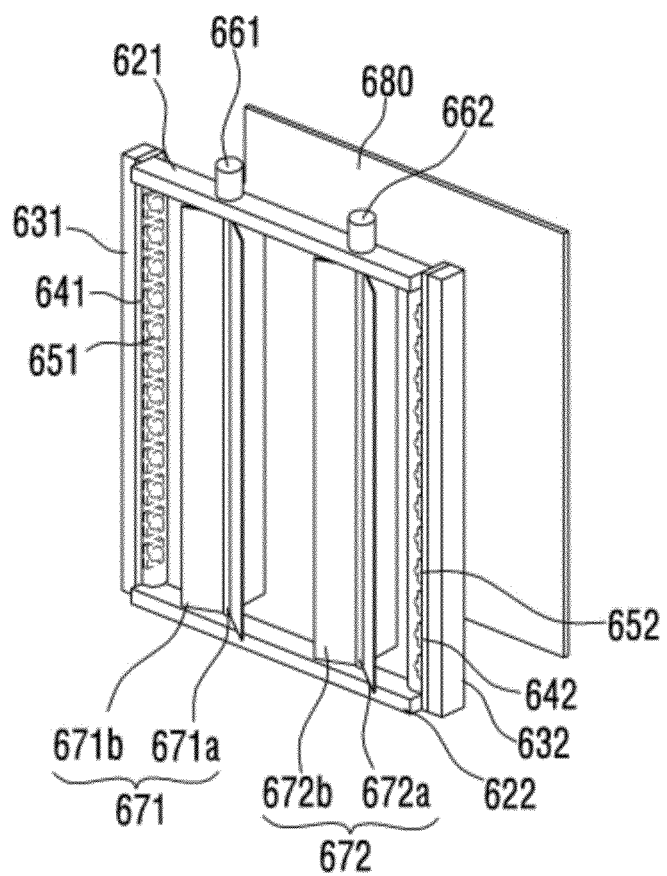
FIG. 19 is a perspective view showing a virus removal device with an ultraviolet LED according to a sixth embodiment.
Figure 20:
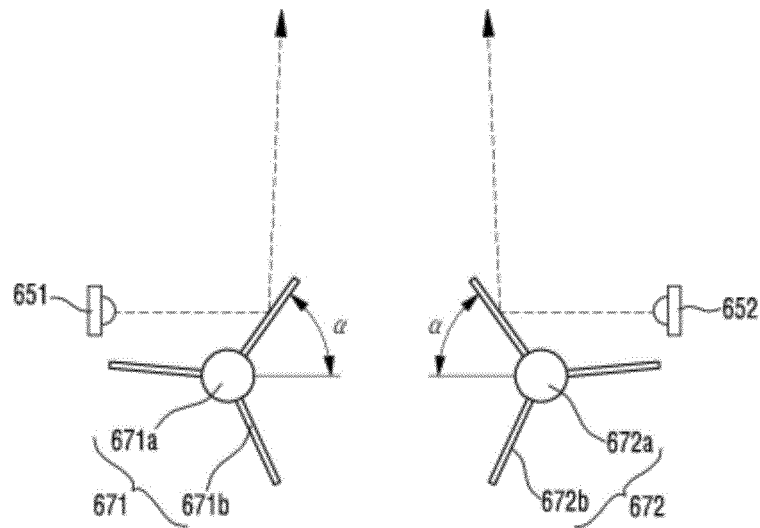
FIG. 20 is a perspective view showing a state where a rotary member of FIG. 19 is rotated by an angle α.
Figure 21:
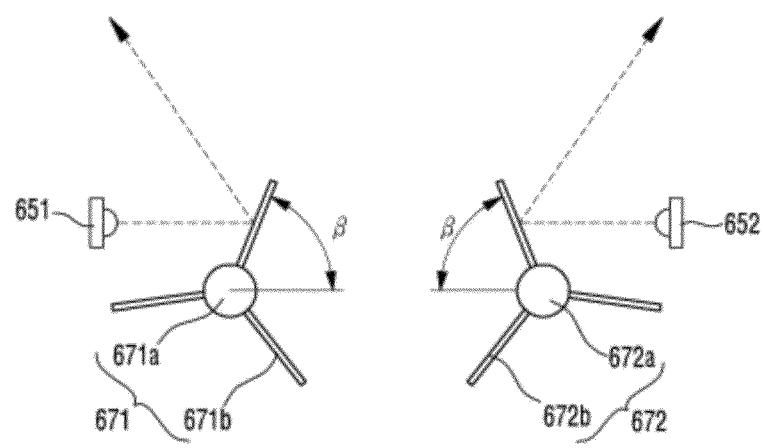
FIG. 21 is a perspective view showing a state where the rotary member of FIG. 19 is rotated by an angle β.

FIG. 19 is a perspective view showing a virus removal device with an ultraviolet LED according to a sixth embodiment. FIG. 20 is a perspective view showing a state where a rotary member of FIG. 19 is rotated by an angle α. FIG. 21 is a perspective view showing a state where the rotary member of FIG. 19 is rotated by an angle β. Referring to FIGS. 2 and 19, the virus removal device may include horizontal members 621 and 622, vertical members 631 and 632, rotary members 671 and 672, base part 641 and 642, heat dissipaters (not shown), ultraviolet LEDs 651 and 652, a diffusion sheet 680 and a driving means.

The horizontal members 621 and 622 are disposed in parallel to each other. First and second motors 661 and 662 are connected to the horizontal members 621 and 622 so as to rotate the rotary members 671 and 672.

The rotary members 671 and 672 are disposed in a direction vertical to the length direction of the horizontal members 621 and 622. The rotary member 671 has a rotary shaft 671a passing through the horizontal members 621 and 622 and rotary plates 671b rotated about the rotary shaft 671a, and the rotary member 672 has a rotary shaft 672a passing through the horizontal members 621 and 622 and rotary plates 672b rotated about the rotary shaft 672a. The rotary members 671 and 672 are disposed in the length direction of an object to be sterilized. One end of each of the rotary shafts 671a and 672a passes through one horizontal member 621, and the other end of each of the rotary shafts 671a and 672a passes through the other horizontal member 622. The rotary plates 671b and 672b are rotated in the state where the one and the other ends of each of the rotary shafts 671a and 672a are come in contact with the respective horizontal members 621 and 622. The vertical members 631 and 632 are disposed at one and the other sides of the horizontal members 621 and 622, respectively. The rotary members 671 and 672 may be disposed at the same distance from the ultraviolet LEDs 651 and 652 respectively disposed on the vertical members 631 and 632. The rotary members 671 and 672 may include the plurality of rotary plates 671b and 672b of which numbers are identical to each other. The rotary plates 671b and 672b may be disposed at the same angle and interval. The rotary plates 671b and 672b may be rotated at the same speed.

A plurality of ultraviolet LEDs 651 and a plurality of ultraviolet LEDs 652 may be disposed in the length direction of the vertical members 631 and 632 at the same interval on the respective vertical members 631 and 632. The ultraviolet LEDs 651 and 652 are disposed in the length direction of the rotary members 671 and 672 so as to irradiate light reflected by the rotary members 671 and 672 onto the object to be sterilized. Specifically, referring to the air conditioner shown in FIG. 2, the ultraviolet LEDs 651 and 652 are disposed on upper surfaces of the base parts 641 and 642 such as PCBs, respectively. The ultraviolet LEDs 551 and 552 are disposed along the vertical length direction of the evaporator 181 based on the drain pan 182 so as to remove microbes or viruses bred in the evaporator 181 and the drain pan 182 for collecting condensation water flowing from surfaces of the evaporator 181 at a lower part of the evaporator 181. The position at which the light generated from the ultraviolet LEDs 651 and 652 reaches the evaporator 181 is changed in a direction vertical to the length direction of the pins 181a depending on time. That is, as shown in FIGS. 20 and 21, light emitted from the ultraviolet LEDs 651 and 652 is reflected from the rotary plates 671b and 672b is reflected and then irradiated toward the evaporator 181. As each of the rotary plates 671b and 672b are rotated, the position at which the light reaches the evaporator 181 is changed in a direction vertical to the length direction of the evaporator 181. When the rotary plates 671b and 672b are rotated at the same speed, the two rotary plates 671b make an angle α with respect to the direction in which the light is irradiated in FIG. 20, and the two rotary plates 672b make an angle 13 with respect to the direction in which the light is irradiated in FIG. 21. In terms of time, the time of the angle β is more taken than that of the angle α. Here, the light is gradually distant from the center of the evaporator 181.

The heat dissipaters (not shown) may be disposed to dissipate heat generated due to the light emission of the ultraviolet LEDs 651 and 652. The heat dissipaters are respectively disposed adjacent to the base parts 641 and 642 disposed beneath the ultraviolet LEDs 651 and 652 below the base parts 641 and 642, so as to dissipate the heat generated from the ultraviolet LEDs 651 and 652. The heat dissipater may be formed of a carbon nanotube (CNT) composite material.

The diffusion sheet 680 diffuses light reflected from the rotary members 671 and 672 toward the object to be sterilized. The diffusion sheet 680 is disposed between the base parts 641 and 642 and the object to be sterilized, so that ultraviolet light can be uniformly thrown on the object to be sterilized as compared with a case where the diffusion sheet 680 is not disposed. Referring to the air conditioner shown in FIG. 2, it is possible to remove even microbes and viruses located at corners of the evaporator 181 and the drain pan 182.

The driving means generates a driving force for rotating the rotary members 617 and 672. The driving means includes the first and second motors 661 and 662 respectively connected to the rotary shafts 671a and 672a of the rotary members 671 and 672 by passing through the horizontal members 621 and 622. The rotary shafts 671a and 672a of the rotary members 671 and 672 are respectively inserted into holes (not shown) formed in the horizontal member 622, so that the rotary shafts 671a and 672a of the rotary members 671 and 672 can be rotated when the first and second motor 661 and 662 rotates, respectively. When the first and second motors 661 and 662 rotate in a positive direction, the rotary members 671 and 672 are rotated in one direction. When the first and second motors 661 and 662 rotate in a reverse direction, the rotary members 671 and 672 are rotated in the opposite direction to the one direction.

Figure 22:
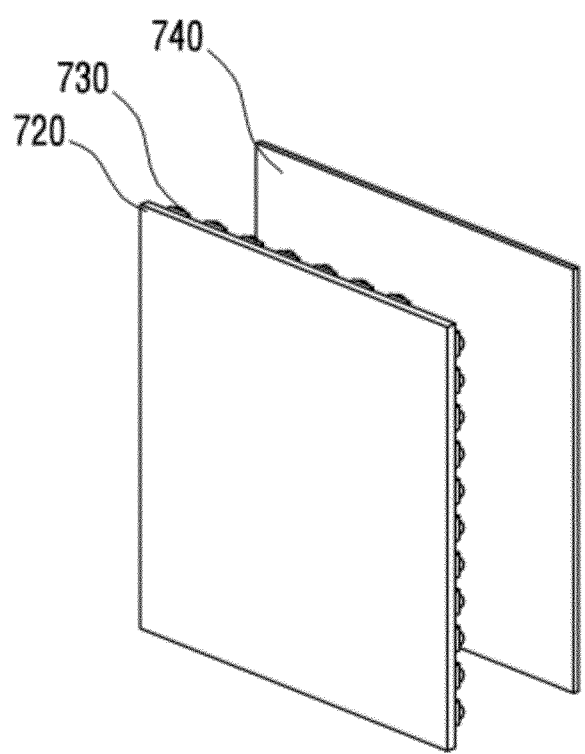
FIG. 22 is a perspective view showing a virus removal device with an ultraviolet LED according to a seventh embodiment.
Figure 23:
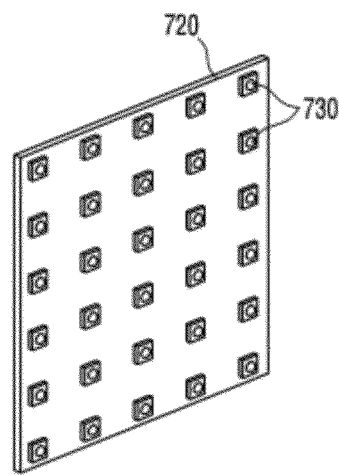
FIG. 23 is a perspective view showing a state where the ultraviolet LED is disposed on a base part of FIG. 22.
Figure 24:
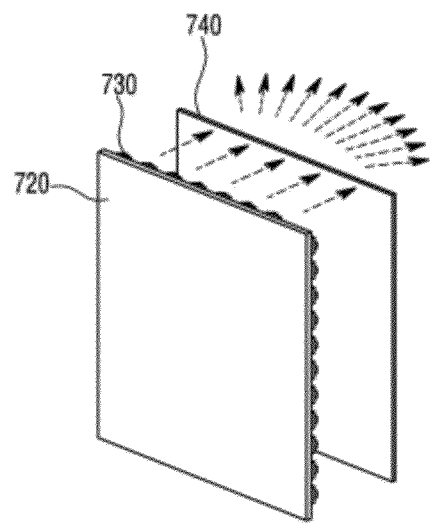
FIG. 24 is a perspective view showing a state where light generated from the ultraviolet LED of FIG. 22 is emitted.

FIG. 22 is a perspective view showing a virus removal device with an ultraviolet LED according to a seventh embodiment. FIG. 23 is a perspective view showing a state where the ultraviolet LED is disposed on a base part of FIG. 22. FIG. 24 is a perspective view showing a state where light generated from the ultraviolet LED of FIG. 22 is emitted. Referring to FIGS. 2 and 22, the virus removal device may include a base part 720, a heat dissipater (not shown), an ultraviolet LED 730 and a diffusion sheet 740.

The base part 720 is disposed in front of an object to be sterilized.

A plurality of ultraviolet LEDs 730 may be disposed on the base part 720. Specifically, the ultraviolet LEDs 730 may be disposed to have a plurality of rows and a plurality of columns on the base part 720 such as a PCB. Referring to the air conditioner shown in FIG. 2, the ultraviolet LEDs 730 removes microbes or viruses bred in the evaporator 181 and the drain pan 182 for collecting condensation water flowing from surfaces of the evaporator 181 at a lower part of the evaporator 181. The ultraviolet LEDs 730 may be symmetrically disposed on one and the other sides of the base part 720, and the ultraviolet LEDs 730 disposed on the one side of the base part 720 may be disposed to have rows and columns at the same interval.

The heat dissipater (not shown) may be disposed to dissipate heat generated due to the light emission of the ultraviolet LED 730. The heat dissipater is disposed adjacent to the base part 720 disposed beneath the ultraviolet LED 730 below the base part 720, so as to dissipate the heat generated from the ultraviolet LED 730. The heat dissipater may be formed of a carbon nanotube (CNT) composite material.

The diffusion sheet 740 diffuses light emitted from the ultraviolet LED 730 toward the object to be sterilized. The diffusion sheet 740 is disposed between the base part and the object to be sterilized, so that ultraviolet light can be uniformly thrown on the object to be sterilized as compared with a case where the diffusion sheet 740 is not disposed. Referring to the air conditioner shown in FIG. 2, it is possible to remove even microbes and viruses located at corners of the evaporator 181 and the drain pan 182.

Figure 25:
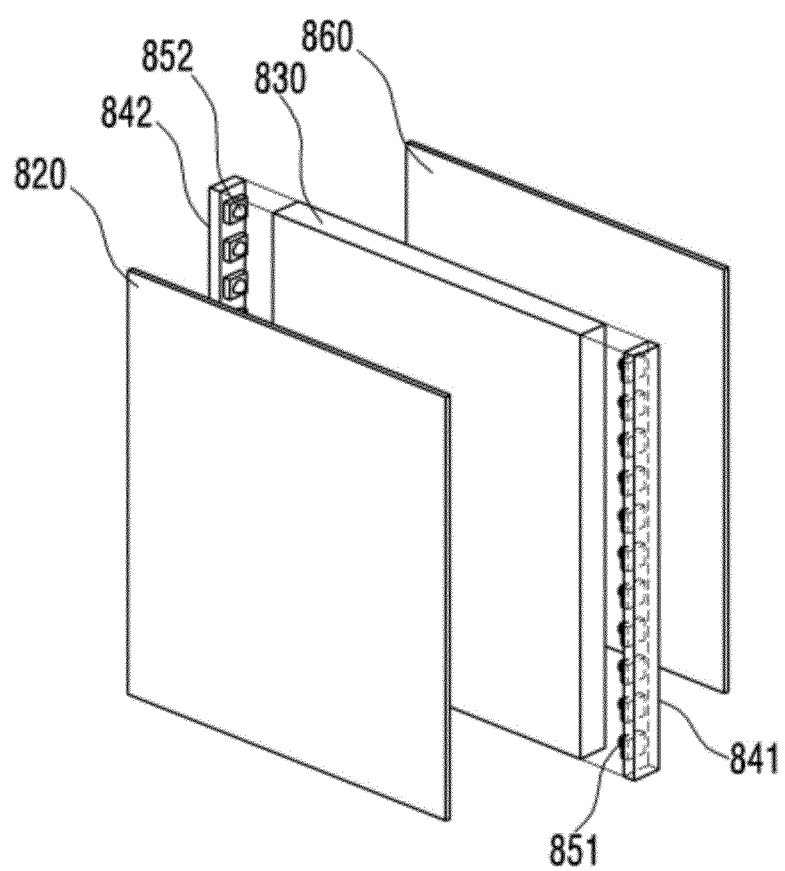
FIG. 25 is a perspective view showing a virus removal device with an ultraviolet LED according to an eighth embodiment.
Figure 26:
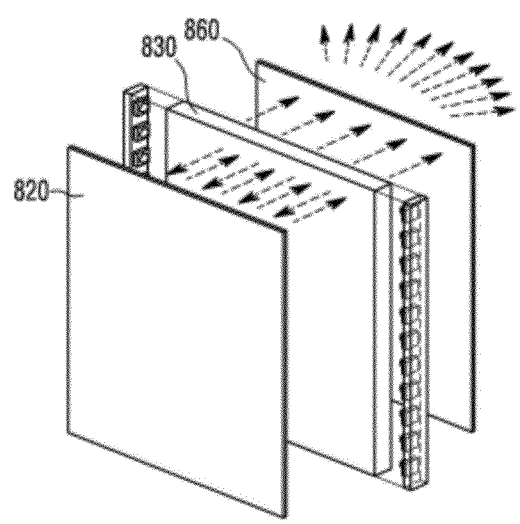
FIG. 26 is a perspective view showing a state where light generated from the ultraviolet LED of FIG. 25 is emitted.

FIG. 25 is a perspective view showing a virus removal device with an ultraviolet LED according to an eighth embodiment. FIG. 26 is a perspective view showing a state where light generated from the ultraviolet LED of FIG. 25 is emitted. Referring to FIG. 25, the virus removal device may include a reflection sheet 820, base parts 841 and 842, a heat dissipater (not shown), ultraviolet LEDs 851 and 852, a light guide plate 830 and a diffusion sheet 860.

The reflection sheet 820 is disposed at one side of the light guide plate 830. When light emitted from the ultraviolet LEDs 851 and 852 is irradiated toward the reflection sheet 820 through the light guide plate 830 as shown in FIG. 26, the reflection sheet 820 reflects light irradiated from the light guide plate 830 so that the reflected light is irradiated toward the object to be sterilized through the light guide plate 830. That is, the reflection sheet 820 reflects light irradiated in other direction except the direction of the object to be sterilized so that the reflected light is irradiated toward the object to be sterilized. Thus, the amount of light irradiated toward the object to be sterilized is increased as compared with a case where the reflection sheet 820 is not disposed.

A plurality of ultraviolet LEDs 851 and a plurality of ultraviolet LEDs 852 may be disposed on one and the other sides of the light guide plate 830. Specifically, the ultraviolet LEDs 851 and 852 are disposed on upper surfaces of the base parts 841 and 842 such as PCBs, respectively. The base parts 841 and 842 having the ultraviolet LEDs 851 and 852 respectively mounted thereon are connected to the light guide plate 830 so that the ultraviolet LEDs 851 and 852 are optically coupled to the light guide plate 830. Referring to the air conditioner shown in FIG. 2, the ultraviolet LEDs 851 and 852 are disposed along the vertical length direction of the evaporator 181 with respect to the drain pan 182 so as to remove microbes or viruses bred in the evaporator 181 and the drain pan 182 for collecting condensation water flowing from surfaces of the evaporator 181 at a lower part of the evaporator 181. The numbers of the ultraviolet LEDs 851 and 852 respectively disposed on the one and the other sides of the light guide plate 830 are identical or similar to each other, and the ultraviolet LEDs 851 and 852 may be disposed symmetric to each other.

The heat dissipater (not shown) may be disposed to dissipate heat generated due to the light emission of the ultraviolet LEDs 851 and 852. The heat dissipater is disposed adjacent to the base parts 841 and 842 disposed beneath the respective ultraviolet LEDs 851 and 852 below the base parts 841 and 842, so as to dissipate the heat generated from the ultraviolet LEDs 851 and 852. The heat dissipater may be formed of a carbon nanotube (CNT) composite material.

The light guide plate 830 is optically coupled with the ultraviolet LEDs 851 and 852, so as to allow light emitted from the ultraviolet LEDs 851 and 852 to be irradiated onto the object to be sterilized. Due to the light emission of the ultraviolet LEDs 851 and 852, light emitted from the light guide plate 830 are simultaneously irradiated toward the reflection sheet 830 and the object to be sterilized as shown in FIG. 26. The light irradiated toward the reflection sheet 820 is reflected from the reflection sheet 820 and then irradiated toward the object to be sterilized through the light guide plate 830.

The diffusion sheet 860 diffuses light passing through the light guide plate 830 toward the object to be sterilized. The diffusion sheet 740 is disposed between the light guide plate 830 and the object to be sterilized, so that ultraviolet light, as shown in FIG. 3, can be uniformly thrown on the object to be sterilized as compared with a case where the diffusion sheet 860 is not disposed. Accordingly, it is possible to remove even microbes and viruses located at corners of the object to be sterilized.

Figure 27:
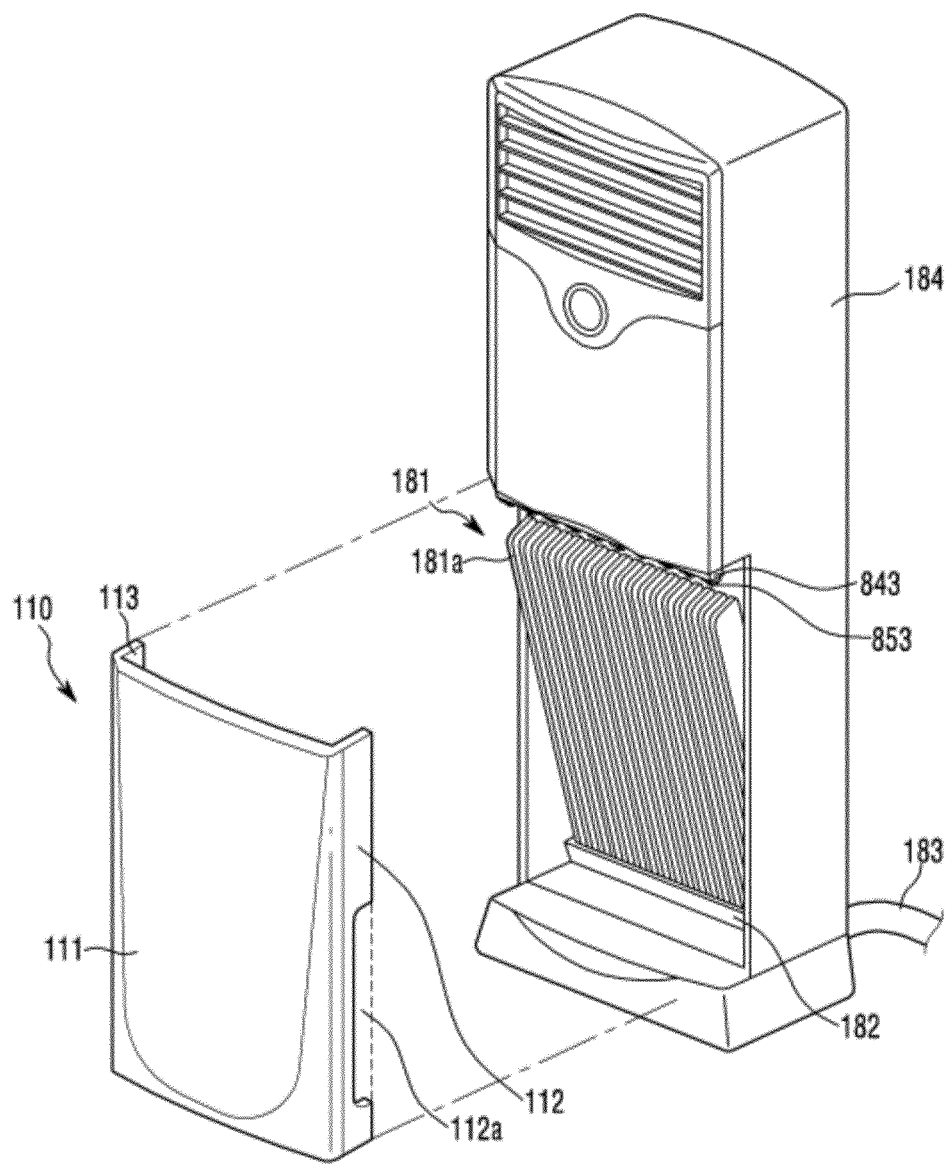
FIG. 27 is an exploded perspective view of the air conditioner to which a virus removal device with an ultraviolet LED is applied according to a ninth embodiment.

FIG. 27 is an exploded perspective view of the air conditioner to which a virus removal device with an ultraviolet LED is applied according to a ninth embodiment. Referring to FIG. 27, the virus removal device may include a base part 843 and an ultraviolet LED 853. In FIG. 27, components identical to those of FIG. 2 are designated by like reference numerals.

The ultraviolet LED 853 is disposed above the evaporator 181 along a direction perpendicular to the length direction of the evaporator 181 that is one of objects to be sterilized, so that light emitted from the ultraviolet LED 853 is irradiated to a lower part of the evaporator 181 toward spaces between the pins 181a of the evaporator 181. Specifically, the ultraviolet LED 853 is disposed on an upper surface of the base part 843 such as a PCB. The ultraviolet LED 853 is disposed along a direction perpendicular to the length direction of the evaporator 181 with respect to the drain pan 182 so as to remove microbes or viruses bred in the evaporator 181 and the drain pan 182 for collecting condensation water flowing from surfaces of the evaporator 181 at a lower part of the evaporator 181. A plurality of ultraviolet LEDs 853 may be disposed at the same interval. That is, since the pins 181a of the evaporator 181 are also disposed at the same interval, the ultraviolet LEDs 853 are necessarily disposed at the same interval so that the light emitted from the ultraviolet LEDs 853 can make a straight advance on the spaces between the pins 181a of the evaporator 181.

A heat dissipater (not shown) may be disposed to dissipate heat generated due to the light emission of the ultraviolet LED 853. The heat dissipater is disposed adjacent to the base part 843 disposed beneath the ultraviolet LED 853 below the base part 843, so as to dissipate the heat generated from the ultraviolet LED 853. The heat dissipater may be formed of a carbon nanotube (CNT) composite material.

Meanwhile, the operation of the air conditioner with the ultraviolet LED 853 according to the ninth embodiment is the same as described in FIG. 2.

Figure 28:
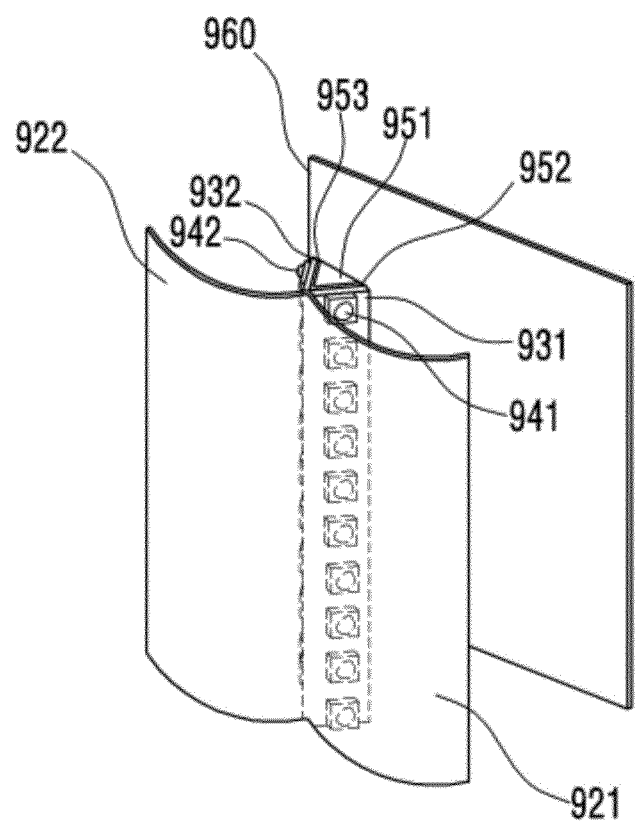
FIG. 28 is a perspective view showing a virus removal device with an ultraviolet LED according to a tenth embodiment.
Figure 29:
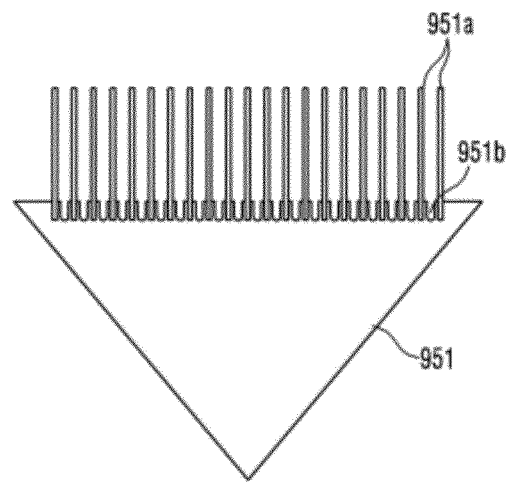
FIG. 29 is a plan view specifically showing a heat dissipater of FIG. 28.
Figure 30:
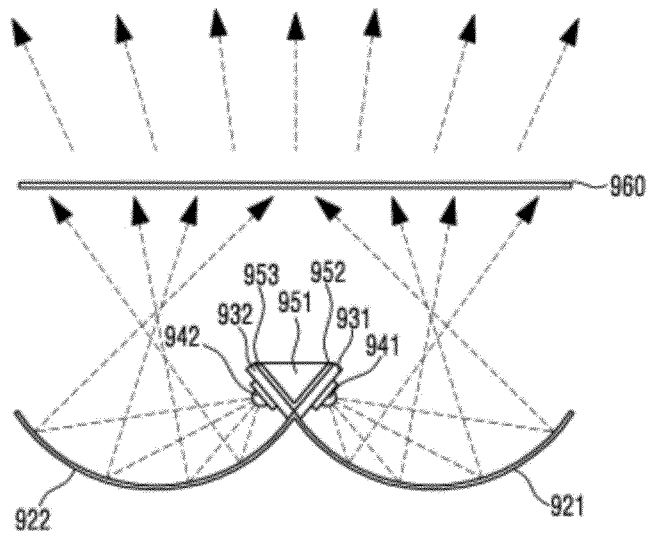
FIG. 30 is a plan view showing a state where a base part of FIG. 28 is disposed.
Figure 31:
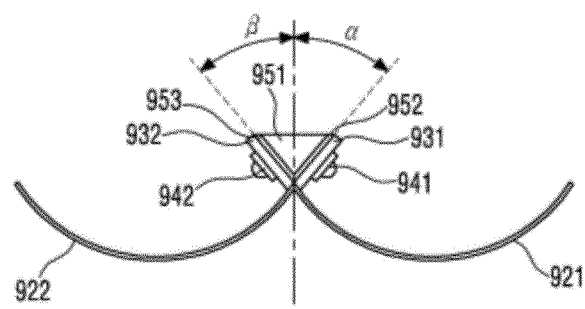
FIG. 31 is a perspective view showing a state where light generated from the ultraviolet LED of FIG. 28 is emitted.

FIG. 28 is a perspective view showing a virus removal device with an ultraviolet LED according to a tenth embodiment. FIG. 29 is a plan view specifically showing a heat dissipater of FIG. 28. FIG. 30 is a plan view showing a state where a base part of FIG. 28 is disposed. FIG. 31 is a perspective view showing a state where light generated from the ultraviolet LED of FIG. 28 is emitted. Referring to FIGS. 2 and 28, the virus removal device may include a first reflector 921, a second reflector 922, a first base part 931, a second base part 932, a first ultraviolet LED 941, a second ultraviolet LED 942, a heat dissipater 951, a first heat dissipation sheet 952, a second heat dissipation sheet 953 and a diffusion sheet 960.

The first reflector 921 has a curved surface. The second reflector 922 is disposed adjacent to one end of the first reflector 921. The curvatures of the curved surfaces of the first and second reflectors 921 and 922 may be identical to each other. Refection surfaces of the first and second reflectors 921 and 922 may be coated with aluminum. When the reflection surface is coated with aluminum, it is possible to increase the reflexibility of the reflection surface.

The first and second base parts 931 and 932 are disposed in directions extended from the first and second reflectors 921 and 922, respectively. As shown in FIG. 31, the first and second base parts 931 and 932 are inclined to the directions of the curved surfaces of the first and second reflectors 921 and 922 so as to have acute angles α and β with respect to a reference surface (indicated by dashed dotted line) for dividing the reflector into the first and second reflectors 921 and 922.

The first reflector 921, the second reflector 922, the first base part 931 and the second base part 932 may be made of the same material. The first reflector 921, the second reflector 922, the first base part 931 and the second base part 932 may be formed in a single body. The first reflector 921, the second reflector 922, the first base part 931 and the second base part 932 are formed in a single body, so that the space of the first reflector 921, the second reflector 922, the first base part 931 and the second base part 932, which occupies in a product having the virus removal device applied thereto, e.g., the air conditioner, is decreased. Thus, the air conditioner does not necessarily become larger than need be. The first and second base parts 931 and 932 are attachable/detachable to/from the first and second reflectors 821 and 922, respectively. The first and second base parts 931 and 932 are attachable/detachable to/from the first and second reflectors 821 and 922, respectively, so that repair and inspection can be easily performed.

The first and second ultraviolet LEDs 941 and 942 are disposed in the length directions of the first and second base parts 931 and 932 on the first and second base parts 931 and 932, respectively, so as to irradiate light reflected from the curved surfaces of the first and second reflectors 921 and 922 toward an object to be sterilized. Specifically, referring to the air conditioner shown in FIG. 2, the first and second ultraviolet LEDs 941 and 942 are disposed on upper surfaces of the first and second base parts 931 and 932 such as PCBs, respectively. The first and second ultraviolet LEDs 941 and 942 are disposed in a vertical length direction of the evaporator 181 with respect to the drain pan 182 so as to remove microbes or viruses bred in the evaporator 181 and the drain pan 182 for collecting condensation water flowing from surfaces of the evaporator 181 at a lower part of the evaporator 181. The numbers of the first and second ultraviolet LEDs 941 and 942 respectively disposed on the upper surfaces of the first and second base parts 931 and 932 may be identical to each other. The first and second ultraviolet LEDs 941 and 942 may be disposed symmetric to each other with respect to a longitudinal center axis of the reflector.

The heat dissipater 951 has a triangular prism shape coming in common contact with lower surfaces of the first and second base parts 931 and 932. Heat generated from the first and second ultraviolet LEDs 941 and 942 is dissipated through a surface not coming in contact with the lower surfaces of the first and second base parts 931 and 932. As shown in FIG. 29, the heat dissipater 951 includes a plurality of heat dissipation pins 951a that are extended from the surface not coming in contact with the lower surfaces of the first and second base parts 931 and 932 and formed at the same interval. A plurality of grooves 951b are formed in parallel to one another in the length direction of the heat dissipater 951 on the surface not coming in contact with the lower surfaces of the first and second base parts 931 and 932. As such, the heat dissipation pins 951a and the grooves 951b are provided to the heat dissipater 951, so that the heat dissipation area of the heat dissipater 951 can be broadened, thereby increasing the heat effect of the heat dissipater 951. The plurality of heat dissipation pins 951a are formed at the same interval, and the plurality of the grooves 951b are formed in parallel to one another, so that the heat dissipation of the heat dissipater 951 can be uniformly performed. The heat dissipater may be formed of a carbon nanotube (CNT) composite material.

The first and second heat dissipation sheets 952 and 953 may be inserted between the first base part 931 and the dissipater 951 and between the second base part 932 and the dissipater 951, respectively.

The diffusion sheet 960 diffuses light reflected from the first and second reflectors 921 and 922 toward the evaporator 181.

Figure 32:
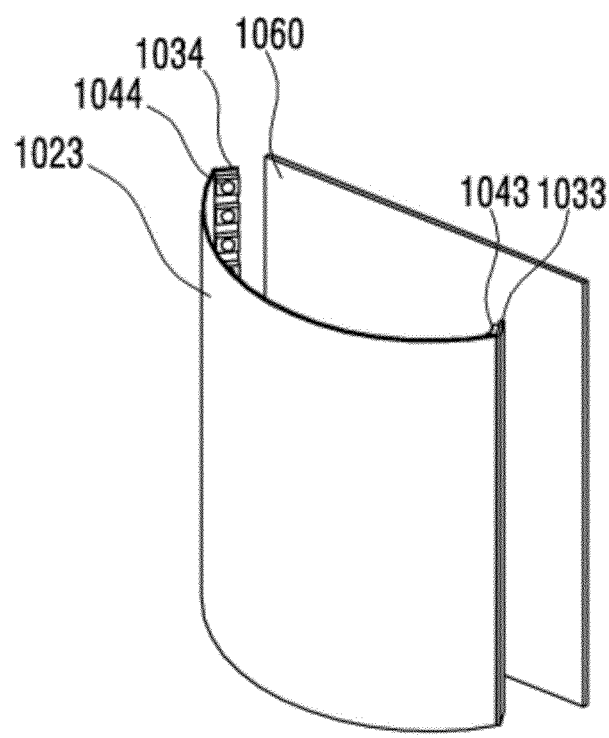
FIG. 32 is a perspective view showing a virus removal device with an ultraviolet LED according to an eleventh embodiment.
Figure 33:
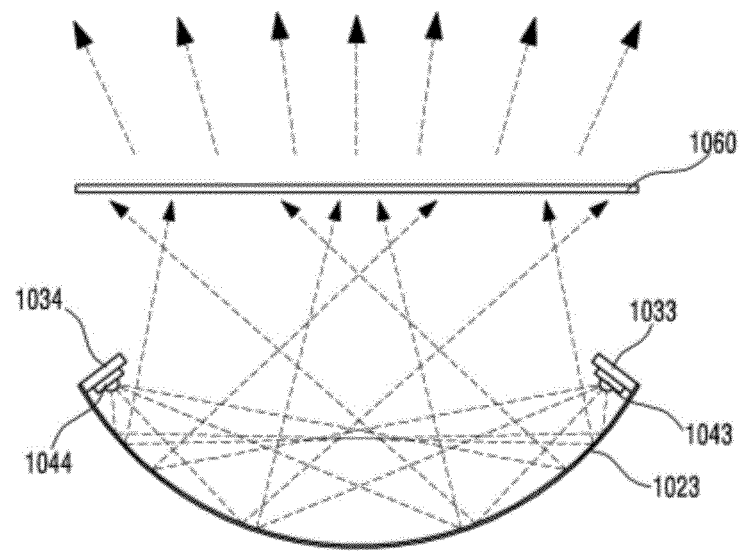
FIG. 33 is a perspective view showing a state where light generated from the ultraviolet LED of FIG. 32 is emitted.

FIG. 32 is a perspective view showing a virus removal device with an ultraviolet LED according to an eleventh embodiment. FIG. 33 is a perspective view showing a state where light generated from the ultraviolet LED of FIG. 32 is emitted. Referring to FIG. 32, the virus removal device may include a reflector 1023, a first base part 1033, a second base part 1034, a first ultraviolet LED 1043, a second ultraviolet LED 1044, a first heat dissipater and a second heat dissipater.

The reflector 1023 has a curved surface. A reflection surface of the reflector 1023 may be coated with aluminum. When the reflection surface of the reflector 1023 is coated with aluminum, it is possible to increase the reflexibility of the reflector 1023.

The first and second base parts 1033 and 1034 are extended from one and the other ends of the reflector 1023 so as to be inclined toward inner curved surfaces of the reflector 1023, respectively.

The reflector 1023, the first base part 1033 and the second base part 1034 may be made of the same material. The reflector 1023, the first base part 1033 and the second base part 1034 may be formed in a single body. The reflector 1023, the first base part 1033 and the second base part 1034 are formed in a single body, so that the space of the reflector 1023, the first base part 1033 and the second base part 1034, which occupies in a product having the virus removal device applied thereto is decreased. Thus, the air conditioner does not necessarily become larger than need be. The first and second base parts 1033 and 1034 are attachable/detachable to/from the reflector 1023. The first and second base parts 931 and 932 are attachable/detachable to/from the reflector 1023, so that repair and inspection can be easily performed.

The first and second ultraviolet LEDs 1043 and 1044 are disposed in the length directions of the first and second base parts 1033 and 1034 on upper surfaces of the first and second base parts 1033 and 1034, respectively, so as to irradiate light reflected from the curved surfaces of the reflector 1023 toward an object to be sterilized. Specifically, the first and second ultraviolet LEDs 1043 and 1044 are disposed on the upper surfaces of the first and second base parts 1033 and 1034 such as PCBs, respectively. At least one of each of the first and second ultraviolet LEDs 1043 and 1044 may be disposed along the vertical or horizontal length direction of the object to be sterilized so as to remove microbes and viruses bred in the object to be sterilized. For example, referring to the air conditioner shown in FIG. 2, at least one of each of the first and second ultraviolet LEDs 1043 and 1044 are disposed along the vertical length direction of the evaporator 181 with respect to the drain pan 182 so as to remove microbes or viruses bred in the evaporator 181 and the drain pan 182 for collecting condensation water flowing from surfaces of the evaporator 181 at a lower part of the evaporator 181. The first and second ultraviolet LEDs 1043 and 1044 respectively disposed on the upper surfaces of the first and second base parts 1033 and 1034 may be disposed to irradiate the same amount of light toward the evaporator 181.

The first and second heat dissipaters are disposed adjacent to lower surfaces of the first and second base parts 1033 and 1034, respectively, so as to dissipate the heat generated from the first and second ultraviolet LEDs 1043 and 1044. The heat dissipaters may be formed of a carbon nanotube (CNT) composite material.

The diffusion sheet 1060 diffuses light reflected from the reflector 1023 toward the object to be sterilized. The diffusion sheet 1060 is disposed forward the reflector 1023, so that ultraviolet light can be uniformly thrown on the object to be sterilized as compared with a case where the diffusion sheet 1060 is not disposed. Referring to the air conditioner shown in FIG. 2, the diffusion sheet 1060 allows ultraviolet light to be uniformly irradiated onto the evaporator 181 and the drain pan 182. Accordingly, it is possible to remove even microbes and viruses located at corners of the evaporator 181 and the drain pan 182.

Meanwhile, the operation of the air conditioner according to the eleventh embodiment is the same as described in FIG. 2.

Figure 34:
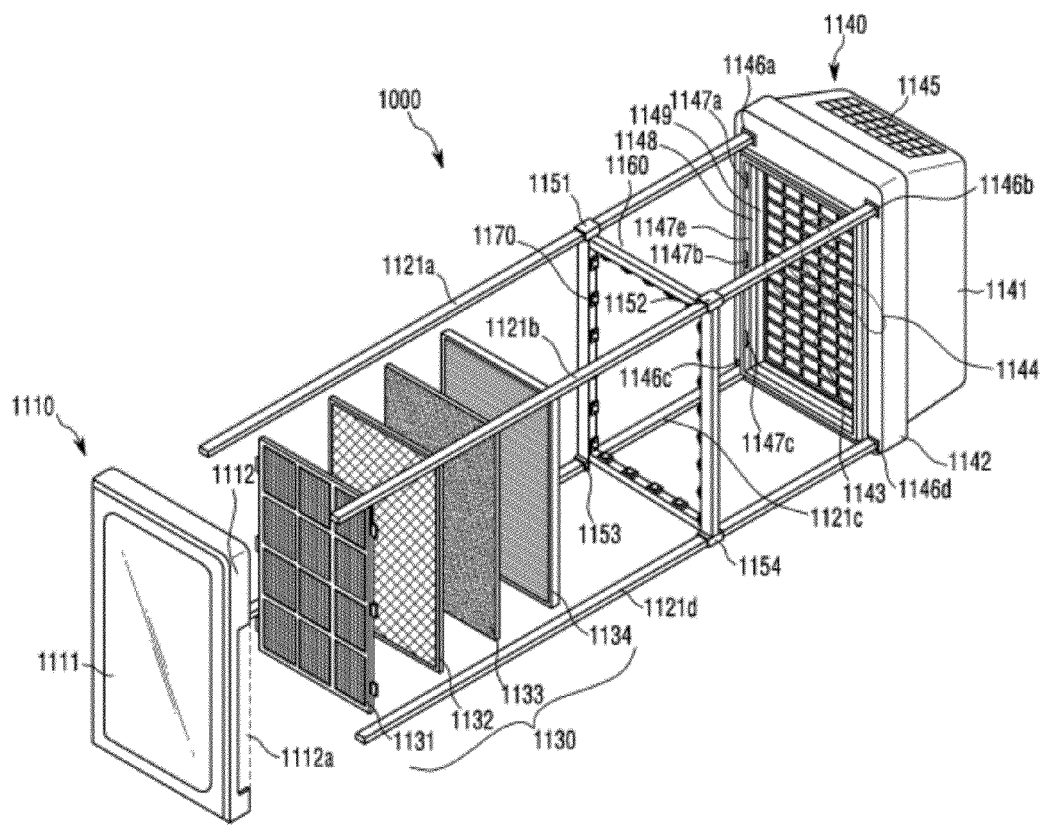
FIG. 34 is an exploded perspective view of an air cleaner to which a virus removal device with an ultraviolet LED is applied according to a twelfth embodiment.

FIG. 34 is an exploded perspective view of an air cleaner to which a virus removal device with an ultraviolet LED is applied according to a twelfth embodiment. Referring to FIG. 34, the air cleaner to which the virus removal device 1000 is applied includes a body part 1140, filters 1130, a cover 1110 and the virus removal device 1000. The virus removal device 1000 includes guide members 1121a, 1121b, 1121c and 1121d, a frame 1160, an ultraviolet LED 1170 and a driving means.

The body part 1140 is composed of a filter accommodation part 1142 that becomes an assembling space of the plurality of filters with respect to an isolation film 1143, and a fan accommodation part 1141 for accommodating a ventilation fan 1144 that allows indoor air to pass through the plurality of filters 1130 and exhausts the purified air to an indoor space. The body part 1140 sucks the indoor air and exhausts the purified air. Exhaustion holes 1145 through which the purified air is exhausted to the indoor space are formed at an upper part of the body part 1140. The exhaustion hole 1145 may be formed in a front, side or rear surface of the body part 1140.

The filters 1130 filter air sucked into the body part 1140 through the exhaustion holes 1145. The plurality of filters 1130 are accommodated in the filter accommodation part 1142. The filters 1130 are composed of a pre-filter 1131, a medium filter 1132, an activated carbon filter 1133 and a HEPA filter 1134, sequentially disposed from the front of the body part 1140. The filters are respectively mounted in pre-filter accommodation grooves 1147a and 1147b and 1147c, a medium filter accommodation groove 1147e, an activated carbon filter accommodation groove 1148 and a HEPA filter accommodation groove 1149, which are formed in the filter accommodation part 1142 of the body part 1140. The pre-filter 1131 is disposed at the foremost side of the filter accommodation part 1142 so as to filter large-sized dust. Although it has described in the twelfth embodiment that the filters 1130 are composed of the pre-filter 1131, the medium filter 1132, the activated carbon filter 1133 and the HEPA filter 1134, the filters 130 may be variously configured.

The cover 1110 constitutes the external appearance of the front surface of the body part 1140. The cover 1110 includes a front part 1111 and guide parts 1112 that are extended in a vertical direction with respect to the front part 1111 and have openings 1112a through which air is sucked at both sides of the front part 1111. The cover 1110 is coupled to the filter accommodation part 1142 and covers the filters 1130 in front of the filters 130, so that the filters 130 are not exposed to the outside. The air sucked through the openings 1112a is sucked in the filters 130.

The guide members 1121a, 1121b, 1121c and 1121d are disposed in parallel to one another at both upper and lower sides of the filters 130. One and the other ends of each of the guide members 1121a, 1121b, 1121c and 1121d is disposed at the body part 1140 and the cover 1110, respectively. That is, the number of the guide members 1121a, 1121b, 1121c and 1121d is four, and four insertion grooves 1146a, 1146b, 1146c and 1146d are formed in each of the body part 1140 and the cover 1110. Here, the one ends of the guide members 1121a, 1121b, 1121c and 1121d are inserted into the respective insertion grooves 1146a, 1146b, 1146c and 1146d formed in one of the body part 1140 and the cover 1110, and the other ends of the guide members 1121a, 1121b, 1121c and 1121d are inserted into the respective insertion grooves 1146a, 1146b, 1146c and 1146d formed in the other of the body part 1140 and the cover 1110.

The frame 1160 has a hollow shape. The frame 1160 has a hollow part moved to left and right in the length direction of the guide members 1121a, 1121b, 1121c and 1121d. For example, the frame 1160 may be implemented as a quadrangular frame. When the frame 1160 is moved toward the filters 1130 from the body part 1140, the HEPA filter 1134, the activated carbon filter 1133, the medium filter 1132 and the pre-filter 1131 sequentially pass through the hollow part of the frame 1160. When the frame 1160 is moved toward the filters 1130 from the cover 1110, the pre-filter 1131, the medium filter 1132, the activated carbon filter 1133 and the HEPA filter 1134 sequentially pass through the hollow part of the frame 1160.

The LED 1170 faces the center of the frame 1160, and is disposed on the frame 1160. The ultraviolet LED 1170 irradiates light onto at least one side surface of the filters 1130 in a direction vertical to the direction in which the front part 1111 faces. The same number of the ultraviolet LEDs 1170 may be disposed on each of the four surfaces facing the center of the frame 1160. The ultraviolet LEDs 1170 may be disposed on each of the four surfaces at the same interval. When the ultraviolet LEDs 1170 are disposed to have the same number or the same interval, the amount of light irradiated onto the filters 1130 can be equalized. When the ultraviolet LED 1170 generates light to be irradiated onto the filters 1130, the position at which the light generated from the ultraviolet LED 1170 reaches the filters 1130 is changed in the length directions of the guide members 1121*a*, 1121*b*, 1121*c* and 1121*d* depending on time.

The driving means is connected to the frame 1160, and generates a driving force while moving along the length directions of the guide members 1121*a*, 1121*b*, 1121*c* and 1121*d* so that the frame 1160 is moved to left and right. The driving means includes first, second, third and fourth motors 1151, 1152, 1153 and 1154 respectively positioned at corner parts of the frame 1160 to move along the length directions of the guide members 1121*a*, 1121*b*, 1121*c* and 1121*d*.

Figure 35:
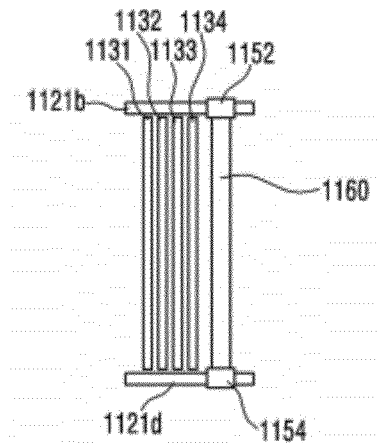
FIG. 35 is a side view showing a state where filters and a frame of FIG. 34 are disposed.

FIG. 35 is a side view showing a state where the filters and the frame of FIG. 34 are disposed. Referring to FIG. 35, the pre-filter 1131, the medium filter 1132, the activated carbon filter 1133 and the HEPA filter 1134 are disposed between the guide members 1121*b* and 1121*d*, and the motors 1152 and 1154 respectively disposed at the guide members 1121*b* and 1121*d* are connected to the frame 1160. One side of the frame 1160 is disposed in parallel to one sides of the pre-filter 1131, the medium filter 1132, the activated carbon filter 1133 and the HEPA filter 1134, and the frame 1160 can be moved along the length direction of the guide members 1121*b* and 1121*d*.

Figure 36:
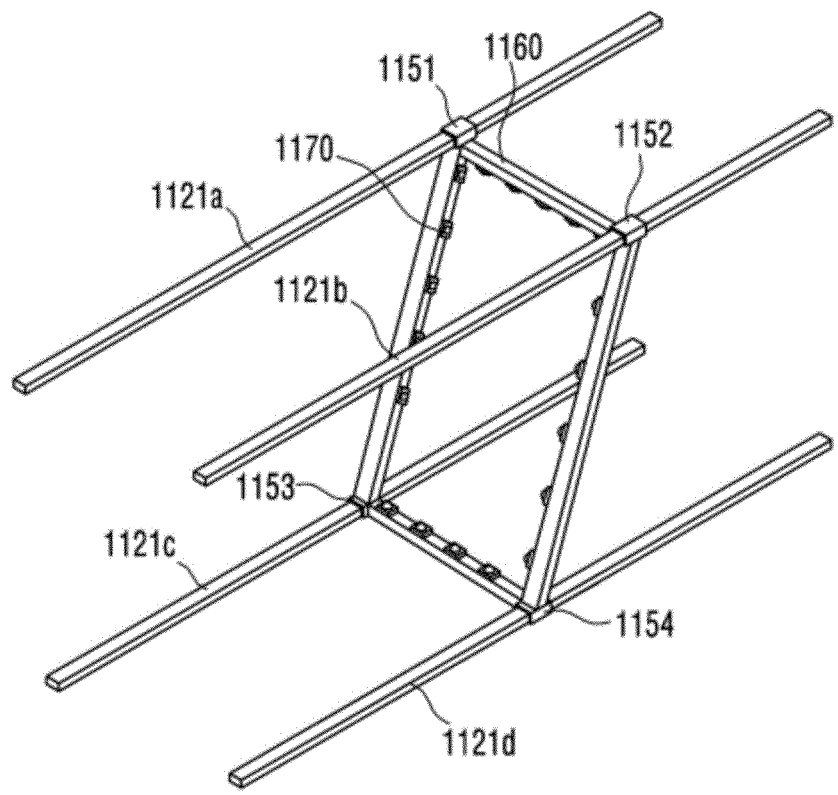
FIG. 36 is a perspective view showing a virus removal device with an ultraviolet LED according to a thirteenth embodiment.

FIG. 36 is a perspective view showing a virus removal device with an ultraviolet LED according to a thirteenth embodiment. Referring to FIGS. 34 and 36, although the one side of the frame 1160 is disposed in parallel to the one sides of the filters 1130 in FIG. 34, the one side of the frame 1160 is disposed to be inclined with respect to the one sides of the filters 1130 in FIG. 36.

As such, when the one side of the frame 1160 is disposed to be inclined with respect to the one sides of the filters 1130, light is simultaneously irradiated onto two or more filters 1130 when the ultraviolet LED 1170 generates the light to be irradiated onto the filters 1130.

Figure 37:
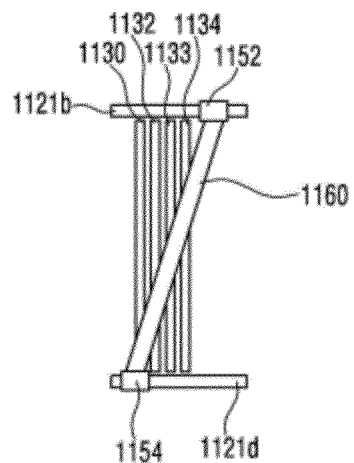
FIG. 37 is a side view showing a state where a filter and a frame of FIG. 36 are disposed.

FIG. 37 is a side view showing a state where a filter and a frame of FIG. 36 are disposed. Referring to FIG. 37, unlike FIG. 35, the one side of the frame 1160 is disposed to be inclined with respect to the one sides of the pre-filter 1131, the medium filter 1132, the activated carbon filter 1133 and the HEPA filter 1134. Thus, when the ultraviolet LED 1170 generates light to be irradiated onto the filters 1130, the light is simultaneously irradiated onto the pre-filter 1131, the medium filter 1132, the activated carbon filter 1133 and the HEPA filter 1134.

Figure 38:
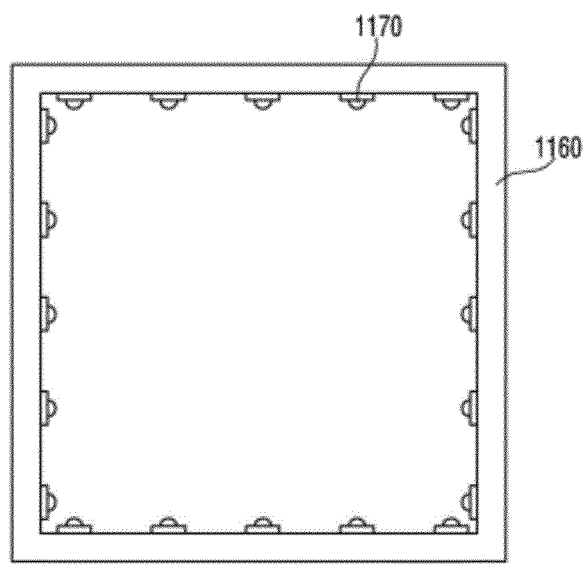
FIG. 38 is a front view of the frame having the ultraviolet LED disposed thereon according to the twelfth and thirteenth embodiments.

FIG. 38 is a front view of the frame having the ultraviolet LED disposed thereon according to the twelfth and thirteenth embodiments. Referring to FIG. 38, the ultraviolet LED 1170 faces the center of the frame 1160, and are disposed on the inner surfaces of the frame 1160.

The same number of the ultraviolet LEDs 1170 may be disposed on each of the four surfaces facing the center of the frame 1160. The ultraviolet LEDs 1170 may be disposed at the same interval on the four surfaces. The ultraviolet LEDs 1170 are disposed to have the same number and the same interval, the amount of light irradiated onto the filters 1130 can be equalized.

Figure 39:
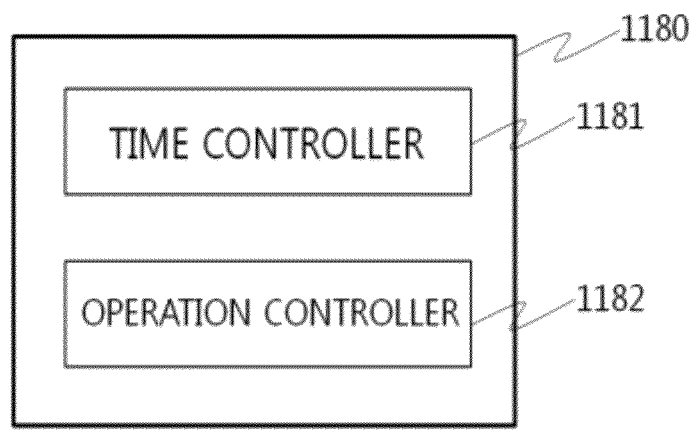
FIG. 39 is a block diagram of a power control device of the air conditioner to which the virus removal device is applied according to the twelfth and thirteenth embodiments.

FIG. 39 is a block diagram of a power control device of the air conditioner to which the virus removal device is applied according to the twelfth and thirteenth embodiments. Referring to FIG. 39, a power control device 1180 includes a time controller 1181 and an operation controller 1182. FIG. 39 will be described together with FIGS. 35 to 38.

In the operation of the ultraviolet LED 1170 of FIGS. 35 to 38, the filters can be sterilized by always turning on the ultraviolet LED 1170, but the ultraviolet LED 1170 may be turned on only for a certain period of time for the purpose of power reduction and energy saving.

That is, the ultraviolet LED 1170 may repeatedly perform an operation of being turned off when a first setup time elapses after the ultraviolet LED 1170 is turned on and being turned on when a second setup time elapses after the ultraviolet LED 1170 is turned off. For example, the ultraviolet LED 1170 may repeatedly perform an operation of being turned off when 30 minutes elapses after the ultraviolet LED 1170 is turned on and being turned on when an hour elapses after the ultraviolet LED 1170 is turned off. The time in the control of the turn-on/turn-off of the ultraviolet LED 1170 is not limited thereto and may be variously set up.

As such, the power control device 1180 may be connected to the ultraviolet LED 1170 so as to control turn-on and turn-off operations of the ultraviolet LED 1170. The power control device 1180 includes a time controller 1181 and an operation controller 1182.

The time controller 1181 counts a time and determines whether or not the counted time correspond to a setup time. The count time unit 1181 does not generate an operation control signal when the counted time does not correspond to the setup time, and generates the operation control signal only when the counted time corresponds to the setup time. Then, the count time unit 1181 transmits the operation control signal to the operation controller 1182. That is, when the counted time corresponds to the setup time, the time controller 1181 continuously generates the operation control signal and transmits the operation control signal to the operation controller 1182. When the counted time does not correspond to the setup time, the time controller 1181 does not generate the operation control signal.

When the counted time corresponds to the setup time, the operation controller 1182 receives the operation control signal from the time controller 1181 and operates the ultraviolet LED 1170. That is, when the counted time corresponds to the setup time, the operation controller 1182 continuously receives the operation control signal from the time controller 1181 and operates the ultraviolet LED 1170. When the counted time elapses and does not correspond to the setup time, the operation controller 1182 does not receive the operation control signal, and therefore cannot operate the ultraviolet LED 1170.

Figure 40:
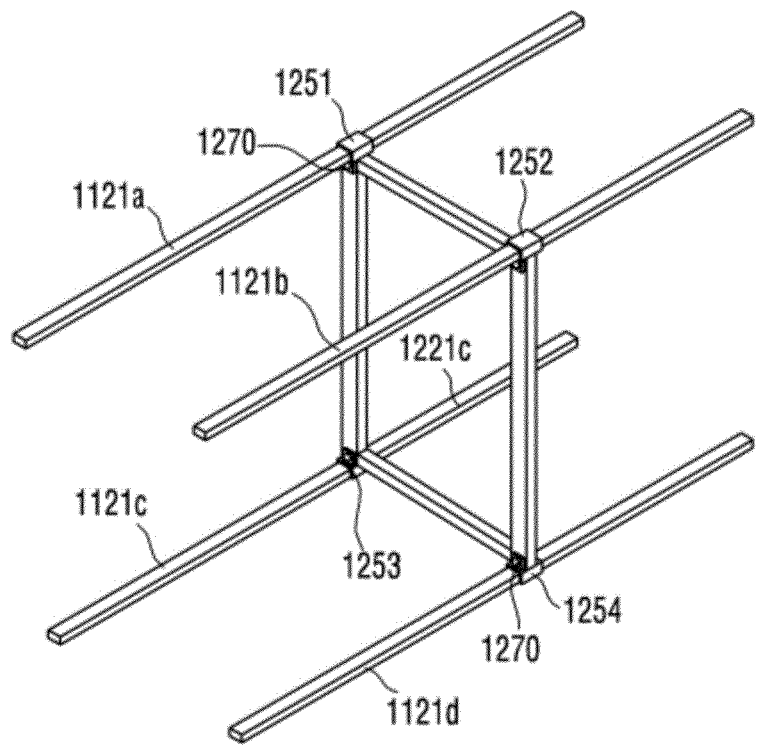
FIG. 40 is a perspective view showing a virus removal device with an ultraviolet LED according to a fourteenth embodiment.

FIG. 40 is a perspective view showing a virus removal device with an ultraviolet LED according to a fourteenth embodiment. Referring to FIGS. 34 and 40, the virus removal device includes guide members 1121*a*, 1121*b*, 1121*c* and 1121*d*, a light guide plate 1260, an ultraviolet LED 1270 and a driving means.

The guide members 1121*a*, 1121*b*, 1121*c* and 1121*d* are disposed in parallel to one another at both upper and lower sides of the filters 130. One and the other ends of each of the guide members 1121a, 1121b, 1121c and 1121d is disposed at the body part 1140 and the cover 1110, respectively. That is, the number of the guide members 1121a, 1121b, 1121c and 1121d is four, and four insertion grooves 1146a, 1146b, 1146c and 1146d are formed in each of the body part 1140 and the cover 1110. Here, the one ends of the guide members 1121a, 1121b, 1121c and 1121d are inserted into the respective insertion grooves 1146a, 1146b, 1146c and 1146d formed in one of the body part 1140 and the cover 1110, and the other ends of the guide members 1121a, 1121b, 1121c and 1121d are inserted into the respective insertion grooves 1146a, 1146b, 1146c and 1146d formed in the other of the body part 1140 and the cover 1110.

The light guide plate 1260 has a hollow shape. The light guide plate 1260 has a hollow part moved to left and right in the length direction of the guide members 1121a, 1121b, 1121c and 1121d. That is, the light guide plate 1260 is moved to left and right with respect to the length direction of the guide member 1112. For example, the light guide plate 1260 may be implemented to have a quadrangular shape. When the light guide plate 11260 is moved toward the filters 1130 from the body part 1140, the HEPA filter 1134, the activated carbon filter 1133, the medium filter 1132 and the pre-filter 1131 sequentially pass through the hollow part of the light guide plate 1260. When the light guide plate 1260 is moved toward the filters 1130 from the cover 1110, the pre-filter 1131, the medium filter 1132, the activated carbon filter 1133 and the HEPA filter 1134 sequentially pass through the hollow part of the light guide plate 1260.

The LEDs 1270 faces in the length direction of the guide members 1121a, 1121b, 1121c and 1121d, and are disposed at corner parts of the light guide plate 1260, respectively on. The ultraviolet LEDs 1270 generate light at corner parts of the light guide plate 1260 to be irradiated onto the filters 1130. As such, the ultraviolet LEDs 1270 are disposed, so that light can be equally radiated toward the filters 1130 from inner sides of the light guide plate 1260. When the ultraviolet LEDs 1270 generate light to be irradiated onto the filters 1130, the position at which the light generated from the ultraviolet LEDs 1270 reaches the filters 1130 is changed in the length directions of the guide members 1121a, 1121b, 1121c and 1121d depending on time.

The driving means is connected to the light guide plate 1260, and generates a driving force while moving along the length directions of the guide members 1121a, 1121b, 1121c and 1121d so that the light guide plate 1260 is moved to left and right. The driving means includes first, second, third and fourth motors 1151, 1152, 1153 and 1154 respectively positioned at corner parts of the light guide plate 1260 to move along the length directions of the guide members 1121a, 1121b, 1121c and 1121d.

Figure 41:
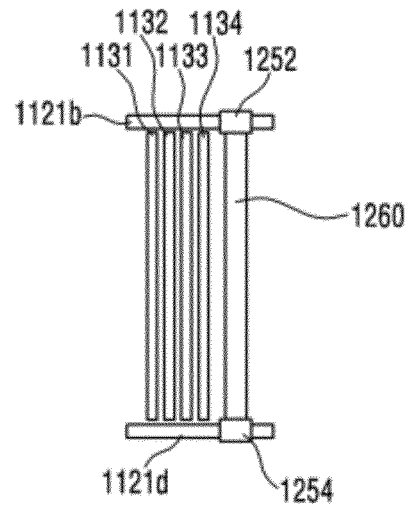
FIG. 41 is a side view showing a state where a filter and a light guide plate of FIG. 40 are disposed.

FIG. 41 is a side view showing a state where a filter and a light guide plate of FIG. 40 are disposed. Referring to FIG. 41, the pre-filter 1131, the medium filter 1132, the activated carbon filter 1133 and the HEPA filter 1134 are disposed between the guide members 1121b and 1121d, and the motors 1152 and 1154 respectively disposed at the guide members 1121b and 1121d are connected to the light guide plate 1260. One side of the light guide plate 1260 is disposed in parallel to one sides of the pre-filter 1131, the medium filter 1132, the activated carbon filter 1133 and the HEPA filter 1134, and the light guide plate 1260 can be moved along the length direction of the guide members 1121b and 1121d.

Figure 42:
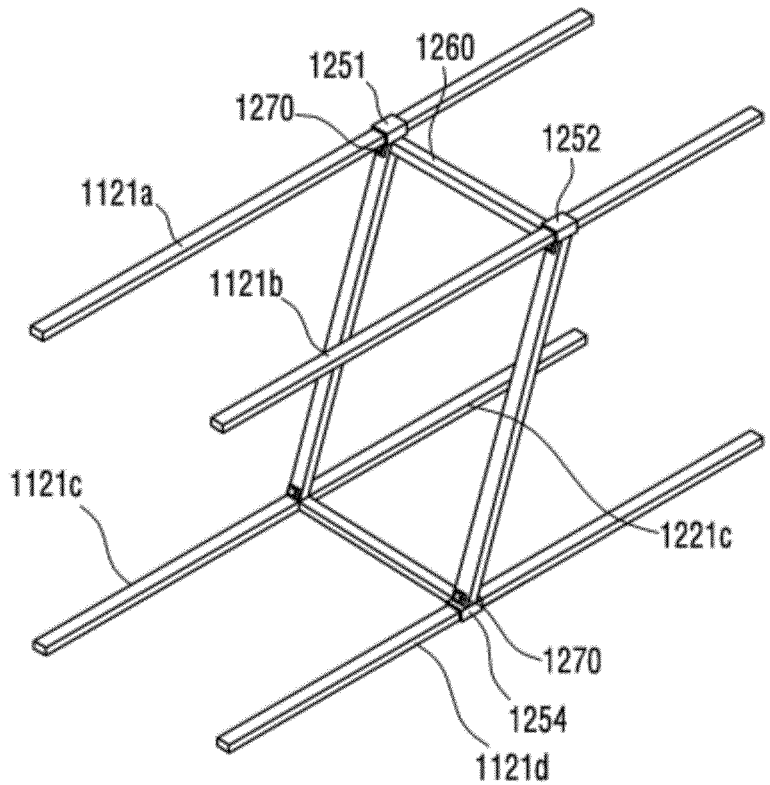
FIG. 42 is a perspective view showing a virus removal device with an ultraviolet LED according to a fifteenth embodiment.

FIG. 42 is a perspective view showing a virus removal device with an ultraviolet LED according to a fifteenth embodiment. Referring to FIG. 42, although the one side of the light guide plate 1260 is disposed in parallel to the one sides of the filters 1130 in FIG. 40, the one side of the light guide plate 1260 is disposed to be inclined with respect to the one sides of the filters 1130 in FIG. 42.

As such, when the one side of the light guide plate 1260 is disposed to be inclined with respect to the one sides of the filters 1130, light is simultaneously irradiated onto two or more filters 1130 when the ultraviolet LED 1270 generate the light to be irradiated onto the filters 1130.

Figure 43:
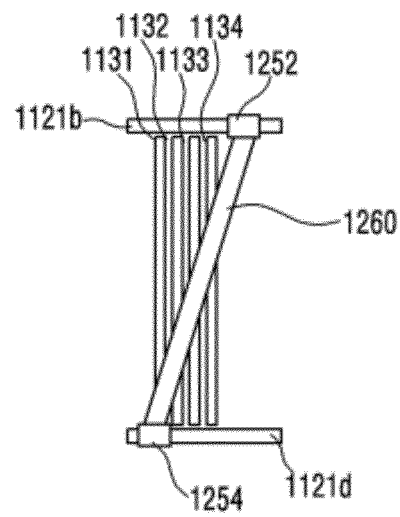
FIG. 43 is a side view showing a state where a filter and a light guide plate of FIG. 42 are disposed.

FIG. 43 is a side view showing a state where a filter and a light guide plate of FIG. 42 are disposed. Referring to FIG. 43, unlike FIG. 41, the one side of the light guide plate 1260 is disposed to be inclined with respect to the one sides of the pre-filter 1131, the medium filter 1132, the activated carbon filter 1133 and the HEPA filter 1134. Thus, when the ultraviolet LED 1270 generates light to be irradiated onto the filters 1130, the light is simultaneously irradiated onto the pre-filter 1131, the medium filter 1132, the activated carbon filter 1133 and the HEPA filter 1134.

Figure 44:
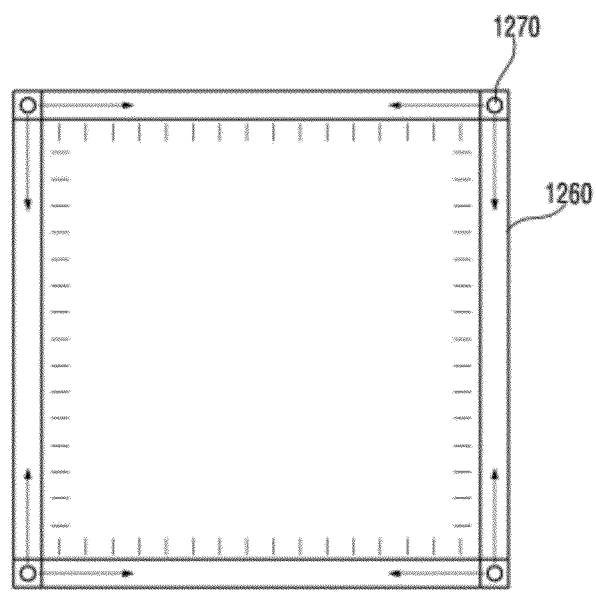
FIG. 44 is a front view of the light guide plate having the ultraviolet LED disposed thereon according to the fourteenth and fifteenth embodiments.

FIG. 44 is a front view of the light guide plate having the ultraviolet LED disposed thereon according to the fourteenth and fifteenth embodiments. Referring to FIG. 44, the ultraviolet LEDs 1270 face the length direction of the guide members 1121b and 1121d, and are disposed at corner parts of the light guide plate 1160, respectively.

The ultraviolet LEDs 1270 generate light from the corner parts of the light guide plate 1260 to be irradiated onto the pre-filter 1131, the medium filter 1132, the activated carbon filter 1133 and the HEPA filter 1134. As such, the ultraviolet LEDs 1270 are disposed, so that light can be equally irradiated toward the pre-filter 1131, the medium filter 1132, the activated carbon filter 1133 and the HEPA filter 1134 from the inner sides of the light guide plate 1260.

According to the embodiments, microbes and viruses bred in an object to be sterilized are effectively removed using an ultraviolet LED, so that it is possible to prevent the microbes and the viruses from being exhausted together with cool air exhausted from an exhaustion gate in an air conditioner or the like. Accordingly, users residing indoors can lead an indoor life more safely and comfortably.

According to the embodiments, since the ultraviolet LED is smaller in size and longer in lifetime than the conventional light sources and converts electric energy directly into light energy, the power consumption of the ultraviolet LED is low, and the efficiency of the ultraviolet LEDs is high. Accordingly, the ultraviolet LED is efficient in removing the microbes and viruses bred in the object to be sterilized.

According to the embodiments, the position at which light generated from the ultraviolet reaches the object to be sterilized is changed depending on time, so that light can be uniformly irradiated onto the object to be sterilized using a few ultraviolet LEDs.

According to the embodiments, a base part with an ultraviolet LED is attachable/detachable to/from a reflector, so that it is possible to easily replace the base part with the ultraviolet LED and to easily maintain and repair the base part with the ultraviolet LED.

According to the embodiments, a reflection surface of the reflector is coated with aluminum, so that it is possible to increase the reflexibility of the reflector.

According to the embodiments, a plurality of pins and a plurality of grooves are provided to a heat dissipater, so that it is possible to ensure a wide heat dissipation area, thereby increasing the heat dissipation effect of the heat dissipater.

According to the embodiments, filters for removing dust or pollutants such as viruses are sterilized using an ultraviolet LED, so that the air cleaning operation of an air cleaner can be smoothly performed.

Any reference in this specification to "one embodiment," "an embodiment," "example embodiment," etc., means that a particular feature, structure, or characteristic described in connection with the embodiment is included in at least one embodiment of the invention. The appearances of such phrases in various places in the specification are not necessarily all referring to the same embodiment. Further, when a particular feature, structure, or characteristic is described in connection with any embodiment, it is submitted that it is within the purview of one skilled in the art to affect such feature, structure, or characteristic in connection with other ones of the embodiments.

Although embodiments have been described with reference to a number of illustrative embodiments thereof, it should be understood that numerous other modifications and embodiments can be devised by those skilled in the art that will fall within the spirit and scope of the principles of this disclosure. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. An air conditioner, comprising:
a cover;
a body part a plurality of filters disposed between the cover and the body part; and
a virus removal device disposed between the cover and the body part,
wherein the virus removal device comprises:
a pair of upper guide members;
a pair of lower guide members;
a moving member having a frame with a hollow portion, each corner of the frame is linked with one of the guide members;
a driving member connected to the frame, and configured to generate a driving force to move the moving member left and right in a length direction of the guide members; and
a plurality of ultraviolet LEDs disposed on the frame, and configured to irradiate ultraviolet light toward a center of the frame.

2. The air conditioner of claim 1, wherein the moving member is configured to be inclined by the driving member to simultaneously sterilize the plurality of filters when the ultraviolet LEDs generate the ultraviolet light onto the filters.

3. The air conditioner of claim 2, wherein the moving member is configured to be inclined by the driving member so that the lower portion of the moving member is disposed more to the left than the upper portion of the moving member, in the length direction of the guide members.

4. The air conditioner of claim 1, wherein the upper and lower guide members are disposed in parallel with each other.

5. The air conditioner of claim 1, wherein the filters are selected from the group consisting of a pre-filter, a medium filter, an activated carbon filter and a high-efficiency particulate arrestance (HEPA) filter.

6. The air conditioner of claim 1, wherein the frame is a quadrangular frame.

7. The air conditioner of claim 1, wherein the driving member comprises first, second, third and fourth motors each respectively positioned at the each corner of the frame.

8. An air conditioner, comprising:
a cover;
a body part;
a plurality of filters disposed between the cover and the body part; and
a virus removal device disposed between the cover and the body part,
wherein the virus removal device comprises:
a pair of upper guide members;
a pair of lower guide members;
a moving member having a light guide frame with a hollow portion, each corner of the light guide frame is linked with one of the guide members;
a driving member connected to the light guide frame, and configured to generate a driving force to move the moving member left and right in a length direction of the guide members; and
a plurality of ultraviolet LEDs disposed on each corner of the light guide frame, and configured to irradiate ultraviolet light toward the each corner of the light guide frame.

9. The air conditioner of claim 8, wherein the moving member is configured to be inclined by the driving member to simultaneously sterilize the plurality of filters when the ultraviolet LEDs generate the ultraviolet light onto the filters.

10. The air conditioner of claim 9, wherein the moving member is configured to be inclined by the driving member so that the lower portion of the moving member is disposed more to the left than the upper portion of the moving member, in the length direction of the guide members.

11. The air conditioner of claim 8, wherein the upper and lower guide members are disposed in parallel with each other.

12. The air conditioner of claim 8, wherein the filters are selected from the group consisting of a pre filer, a medium filter, an activated carbon filter and a high-efficiency particulate arrestance (HEPA) filter.

13. The air conditioner of claim 8, wherein the light guide frame is a quadrangular frame.

14. The air conditioner of claim 8, wherein the driving member comprises first, second, third and fourth motors each respectively positioned at the each corner of the light guide frame.

* * * * *